(12) United States Patent
Honda et al.

(10) Patent No.: US 11,673,929 B2
(45) Date of Patent: Jun. 13, 2023

(54) CYCLIZED CYTOKINES AND METHOD FOR PRODUCING SAME

(71) Applicant: National Institute of Advanced Industrial Science and Technology, Tokyo (JP)

(72) Inventors: Shinya Honda, Tsukuba (JP); Takamitsu Miyafusa, Tsukuba (JP)

(73) Assignee: National Institute of Advanced Industrial Science and Technology, Tokyo (JP)

(*) Notice: Subject to any disclaimer, the term of this patent is extended or adjusted under 35 U.S.C. 154(b) by 1357 days.

(21) Appl. No.: 16/046,276

(22) Filed: Jul. 26, 2018

(65) Prior Publication Data

US 2018/0346539 A1 Dec. 6, 2018

Related U.S. Application Data

(62) Division of application No. 15/566,365, filed as application No. PCT/JP2016/061923 on Apr. 13, 2016, now abandoned.

(30) Foreign Application Priority Data

Apr. 13, 2015 (JP) .................................. 2015-082018

(51) Int. Cl.
| | |
|---|---|
| A61K 38/22 | (2006.01) |
| C07K 14/535 | (2006.01) |
| C07K 1/02 | (2006.01) |
| C12P 21/02 | (2006.01) |
| C12N 5/10 | (2006.01) |
| C07K 19/00 | (2006.01) |
| A61P 7/00 | (2006.01) |
| C12N 15/70 | (2006.01) |
| A61K 38/00 | (2006.01) |

(52) U.S. Cl.
CPC ............ *C07K 14/535* (2013.01); *A61K 38/22* (2013.01); *A61P 7/00* (2018.01); *C07K 1/02* (2013.01); *C07K 19/00* (2013.01); *C12N 5/10* (2013.01); *C12N 15/70* (2013.01); *C12P 21/02* (2013.01); *A61K 38/00* (2013.01); *C12N 2840/445* (2013.01)

(58) Field of Classification Search
None
See application file for complete search history.

(56) References Cited

U.S. PATENT DOCUMENTS

| | | | |
|---|---|---|---|
| 4,033,940 A | 7/1977 | Hughes et al. | |
| 4,102,877 A | 7/1978 | Nutt | |
| 4,810,643 A | 3/1989 | Souza | |
| 5,104,651 A | 4/1992 | Boone et al. | |
| 5,824,778 A | 10/1998 | Ishikawa et al. | |
| 5,985,265 A | 11/1999 | Kinstler et al. | |
| 7,846,710 B2 | 12/2010 | Benkovic et al. | |
| 8,940,501 B2 | 1/2015 | Ploegh et al. | |

FOREIGN PATENT DOCUMENTS

| | | |
|---|---|---|
| JP | 2008-501623 | 1/2008 |
| WO | 2005/044839 | 5/2005 |
| WO | 2010087994 | 8/2010 |

OTHER PUBLICATIONS

Weiss, Michael A.; "THe structure and function of insulin: decoding the tr transition." Vitam. Horm. (2009) 80 p. 33-49.*
Lowe, Derek; "The clinic speaks slowly, and quietly." blog "In the Pipeline," entry of Oct. 7, 2022.*
Howes, Laura; "Deepmind ai predicts protein structures." C&EN, issue of Dec. 1, 2020.*
Eldin, Kareem et al; "Complete sequencing of the recombinatn granulocyte colony stimulating factor (filgrastim) and detection of biotinylation by mass spectroscopy." Amino Acids (2010) 38 p. 1043-1049.*
Young, Dennis C. et al; "Characterization of the receptor binding determinants of grnaulocyte colony stimulating factor." Prot. Sci. (1997) 6 p. 1228-1236.*
Reidhaar-Olson, John F. et al; "Identification of residues critical to the activity of human granulocyte colony stimulating factor." Biochemistry (1996) 35 p. 9034-9041.*
Jiang et al; "Effect of a structurally modified human granulocyte colony stimulating factor, G-CSFa on leukopenia in mice and monkeys." J. Hemaotl. Oncol. (2011) 4(28).*
Japanese Office Action corresponding to Japanese Patent Application No. 201751263, 8 pages, dated Oct. 26, 2018 (English Translation).
Kuga T et al. Mutagenesis of human granulocyte colony stimulating factor. Biochemical and Biophysical Research Communications. Feb. 28, 1989; 159(1): 103-111.
Lord BI et al. Kinetics of neutrophil production in normal and neutropenic animals during the response to filgrastim (r-metHu G-CSF) or filgrastim SD/01 (PEG-r-metHu G-CSF). Clinical Cancer Research. Jul. 2001; 7: 2085-2090.

(Continued)

*Primary Examiner* — Fred H Reynolds
(74) *Attorney, Agent, or Firm* — Myers Bigel, P.A.

(57) ABSTRACT

The purpose of the present invention is to provide a method for producing a very stable, cyclized mutant protein such that high cyclization efficiency is achieved while the number of amino acids added is minimal and the biological properties of an original protein are maintained. In view of conformational information about the original protein, secondary structure-free regions at N/C terminal portions are deleted. Then, a protein database is screened for proteins with secondary structures similar to those of N/C terminal residues of a secondary structure-forming portion after the deletion. The screening results are used to determine the amino acid length of a loop structure through which the N-terminus and the C-terminus of the secondary structure-forming portion of the original protein are to be connected. A cyclized mutant protein is finally produced having a loop structure with the determined amino acid length.

5 Claims, 8 Drawing Sheets

Specification includes a Sequence Listing.

(56) References Cited

OTHER PUBLICATIONS

Oshima Y et al. Biological activity of human granulocyte colony stimulating factor with a modified C-terminus. Biochemical and Biophysical Research Communications. 2000; 267: 924-927.

Popp MW et al. Sortase-catalyzed transformations that improve the properties of cytokines. PNAS. Feb. 22, 2011; 108(8): 3169-3174.

Schumann FH et al. Changing the topology of protein backbone: the effect of backbone cyclization on the structure and dynamics of a SH3 domain. Frontiers in Chemistry. Apr. 8, 2015; 3, article 26, pp. 1-15.

U.S. Department of Health and Human Services, Food and Drug Administration, Guidance for Industry. Immonogenicity assessment for therapeutic protein products. Aug. 2014: 1-36.

Van Der Auwera P et al. Pharmacodynamics and pharmacokinetics of single doses of subcutaneous pegylated human G-CSF mutant (Ro 25-8315) in healthy volunteers: comparison with single and multiple daily doses of filgrastim. American Journal of Hematology. 2001; 66: 245-251.

Van Lieshout JFT et al. Thermal stabilization of an endoglucanase by cyclization. Appl. Biochem. Biotechnol. 2012; 167(7): 2039-2053.

Written Opinion of the International Searching Authority, PCT/JP2016/061923, dated Jul. 19, 2016.

Aboye TL and Camarero JA. Biological synthesis of circular polypeptides. Journal of Biological Chemistry. Aug. 2012; 287(32): 27026-27032.

Antos JM et al. A straight path to circular proteins. Journal of Biological Chemistry. Jun. 2009; 284(23): 16028-16036.

Cheriyan M and Perler FB. Protein splicing: a versatile tool for drug discovery. Advanced drug delivery reviews. 2009; 61: 899-907.

Hill CP et al. The structure of granulocyte-colony-stimulating factor and its relationship to other growth factors. Proc. Natl. Acad. Sci. USA. Jun. 1993; 90: 5167-5171.

Joo SH. Cyclic peptides as therapeutic agents and biochemical tools. Biomolecules & Therapeutics. 2012; 20(1): 19-26.

Pelegri-Oday EM et al. Therapeutic protein-polymer conjugates: advancing beyond PEGylation. J. Am. Chem. Soc. Sep. 2014; 136: 14323-14332.

Wood DW and Camarero JA. Intein applications: from protein purification and labeling to metabolic control methods. Journal of Biological Chemistry. May 2014; 289(21): 14512-14519.

* cited by examiner

[Figure 1]

```
                                      ┌─────── helix A ───────┐      ┌──┐
filgrastim  -MTPLGPASSLPQSFLLKCLEQVRKIQGDGAALQEKLCATYKLCHPEELVLLGHSLGIPW
linear      -MAPLGPASSLPQSFLLKSLEQVRKIQGDGAALQEKLCATYKLCHPEELVLLGHSLGIPW
C177        SMAPLGPASSLPQSFLLKSLEQVRKIQGDGAALQEKLCATYKLCHPEELVLLGHSLGIPW
C170        ----SGPASSLPQSFLLKSLEQVRKIQGDGAALQEKLCATYKLCHPEELVLLGHSLGIPW
C166        --------SSLPQSFLLKSLEQVRKIQGDGAALQEKLCATYKLCHPEELVLLGHSLGIPW
C163        ----------SQSFLLKSLEQVRKIQGDGAALQEKLCATYKLCHPEELVLLGHSLGIPW
             .*****.****************************************************

┌── helix B ──┐     ┌── helix C ──┐
filgrastim  APLSSCPSQALQLAGCLSQLHSGLFLYQGLLQALEGISPELGPTLDTLQLDVADFATTIW
linear      APLSSCPSQALQLAGCLSQLHSGLFLYQGLLQALEGISPELGPTLDTLQLDVADFATTIW
C177        APLSSCPSQALQLAGCLSQLHSGLFLYQGLLQALEGISPELGPTLDTLQLDVADFATTIW
C170        APLSSCPSQALQLAGCLSQLHSGLFLYQGLLQALEGISPELGPTLDTLQLDVADFATTIW
C166        APLSSCPSQALQLAGCLSQLHSGLFLYQGLLQALEGISPELGPTLDTLQLDVADFATTIW
C163        APLSSCPSQALQLAGCLSQLHSGLFLYQGLLQALEGISPELGPTLDTLQLDVADFATTIW
            ************************************************************

┌──┐             ┌──────── helix D ────────┐
filgrastim  QQMEELGMAPALQPTQGAMPAFASAFQRRAGGVLVASHLQSFLEVSYRVLRHLAQP-
linear      QQMEELGMAPALQPTQGAMPAFASAFQRRAGGVLVASHLQSFLEVSYRVLRHLAQP-
C177        QQMEELGMAPALQPTQGAMPAFASAFQRRAGGVLVASHLQSFLEVSYRVLRHLAQPG
C170        QQMEELGMAPALQPTQGAMPAFASAFQRRAGGVLVASHLQSFLEVSYRVLRHLG---
C166        QQMEELGMAPALQPTQGAMPAFASAFQRRAGGVLVASHLQSFLEVSYRVLRHLG---
C163        QQMEELGMAPALQPTQGAMPAFASAFQRRAGGVLVASHLQSFLEVSYRVLRHLG---
            ****************************************************.
```

[Figure 2]

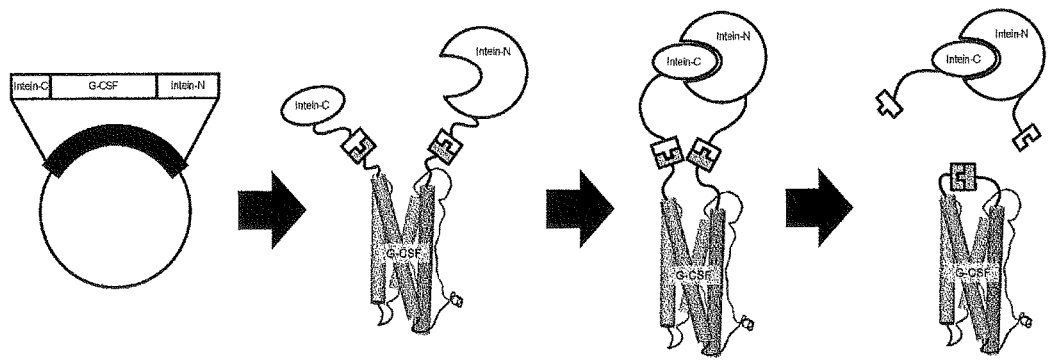

[Figure 3]
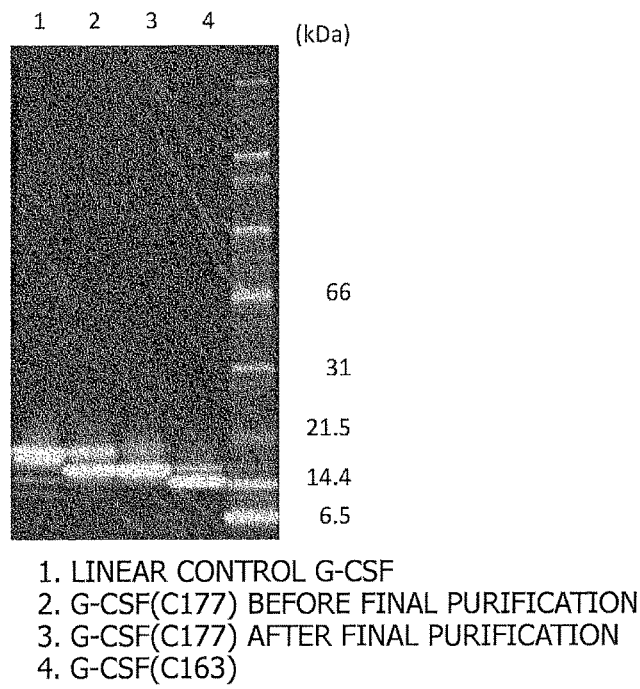
1. LINEAR CONTROL G-CSF
2. G-CSF(C177) BEFORE FINAL PURIFICATION
3. G-CSF(C177) AFTER FINAL PURIFICATION
4. G-CSF(C163)
[Figure 4]
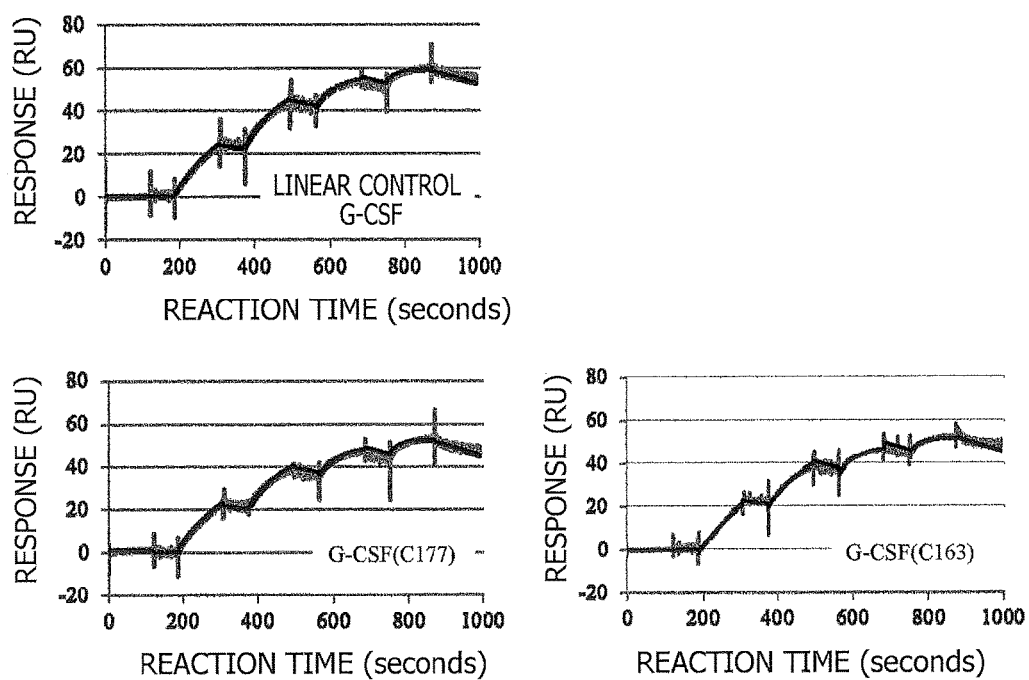

[Figure 5]
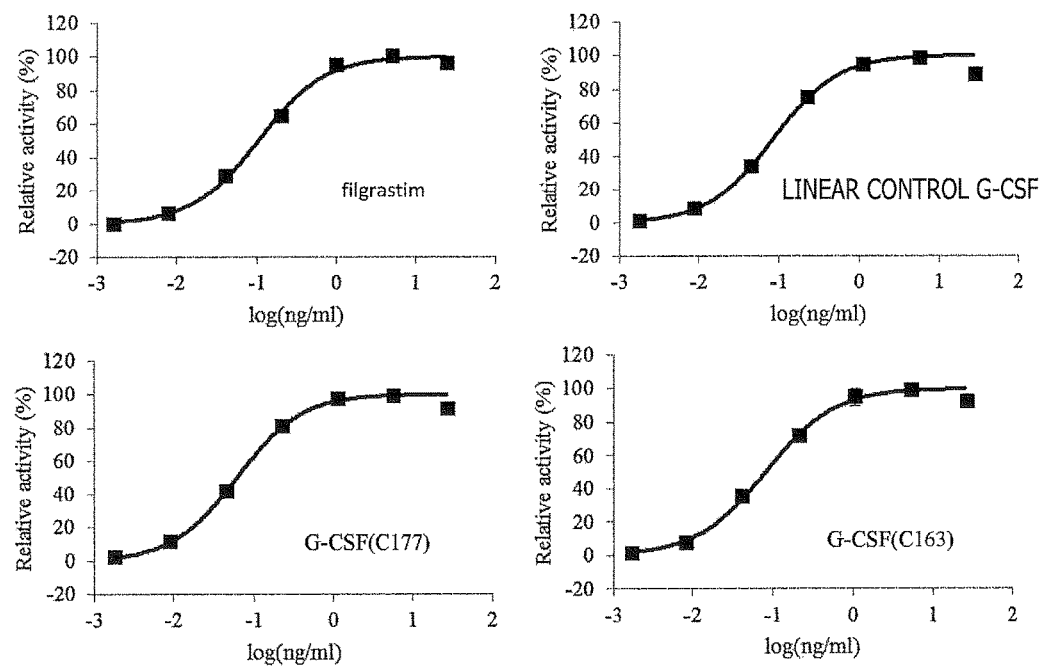
[Figure 6]
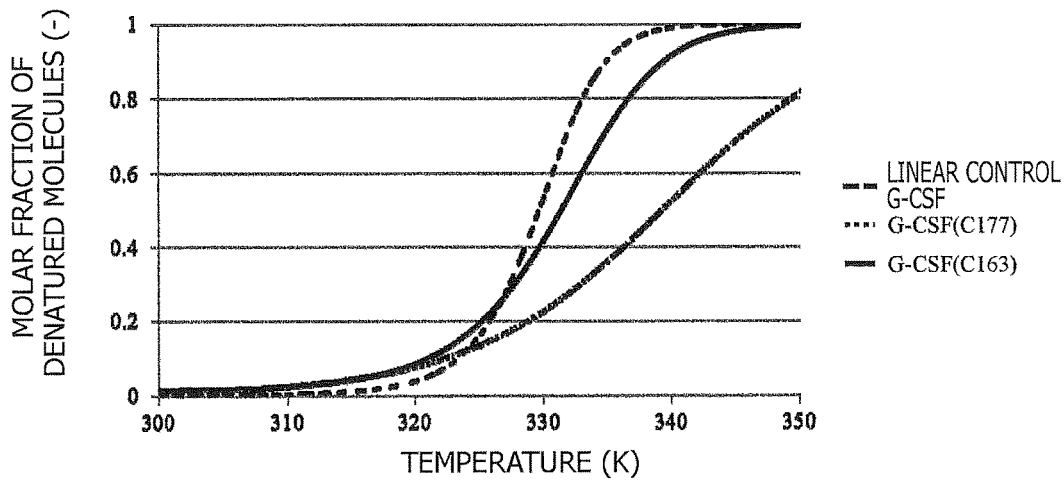

[Figure 7]
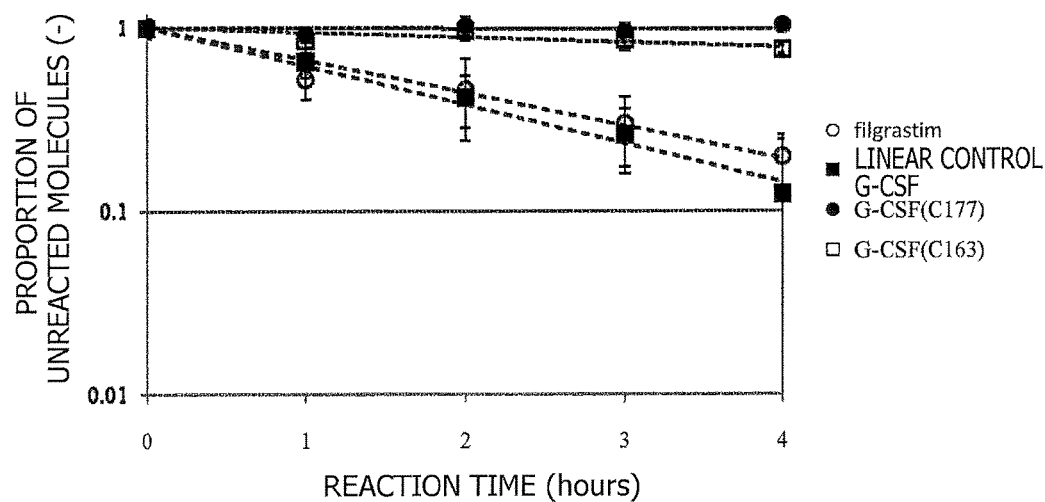
[Figure 8]
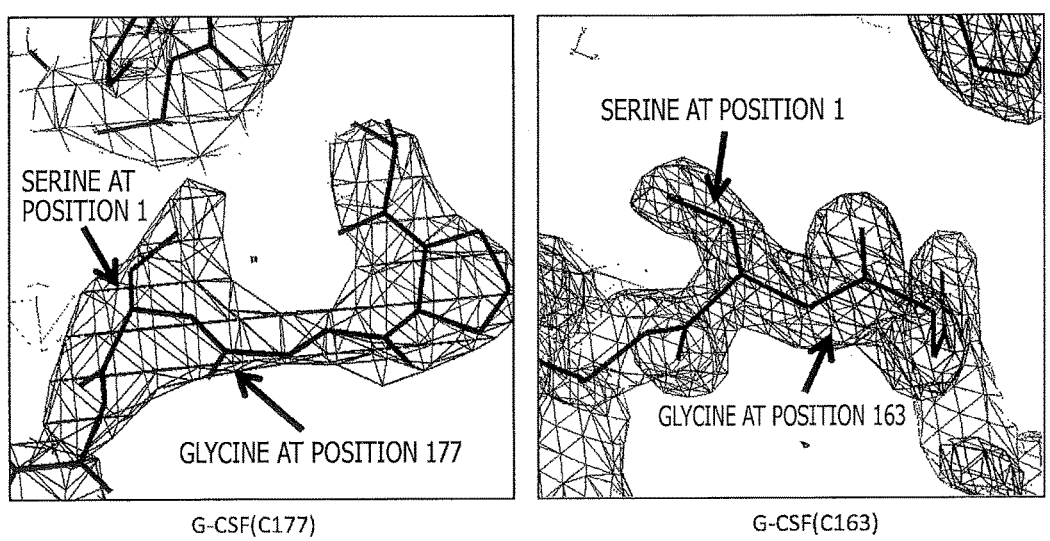

[Figure 9]
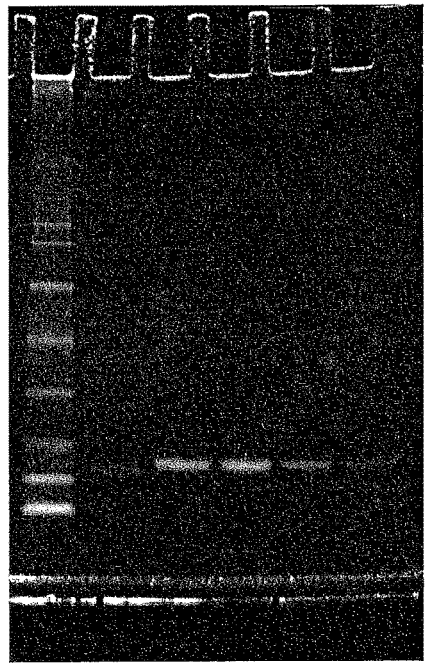
G-CSF(C170)
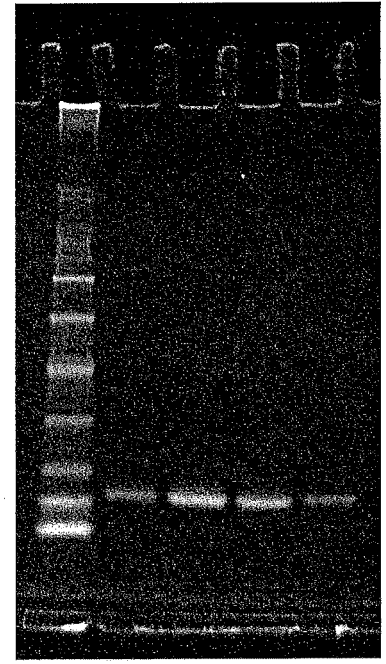
G-CSF(C166)

[Figure 10]
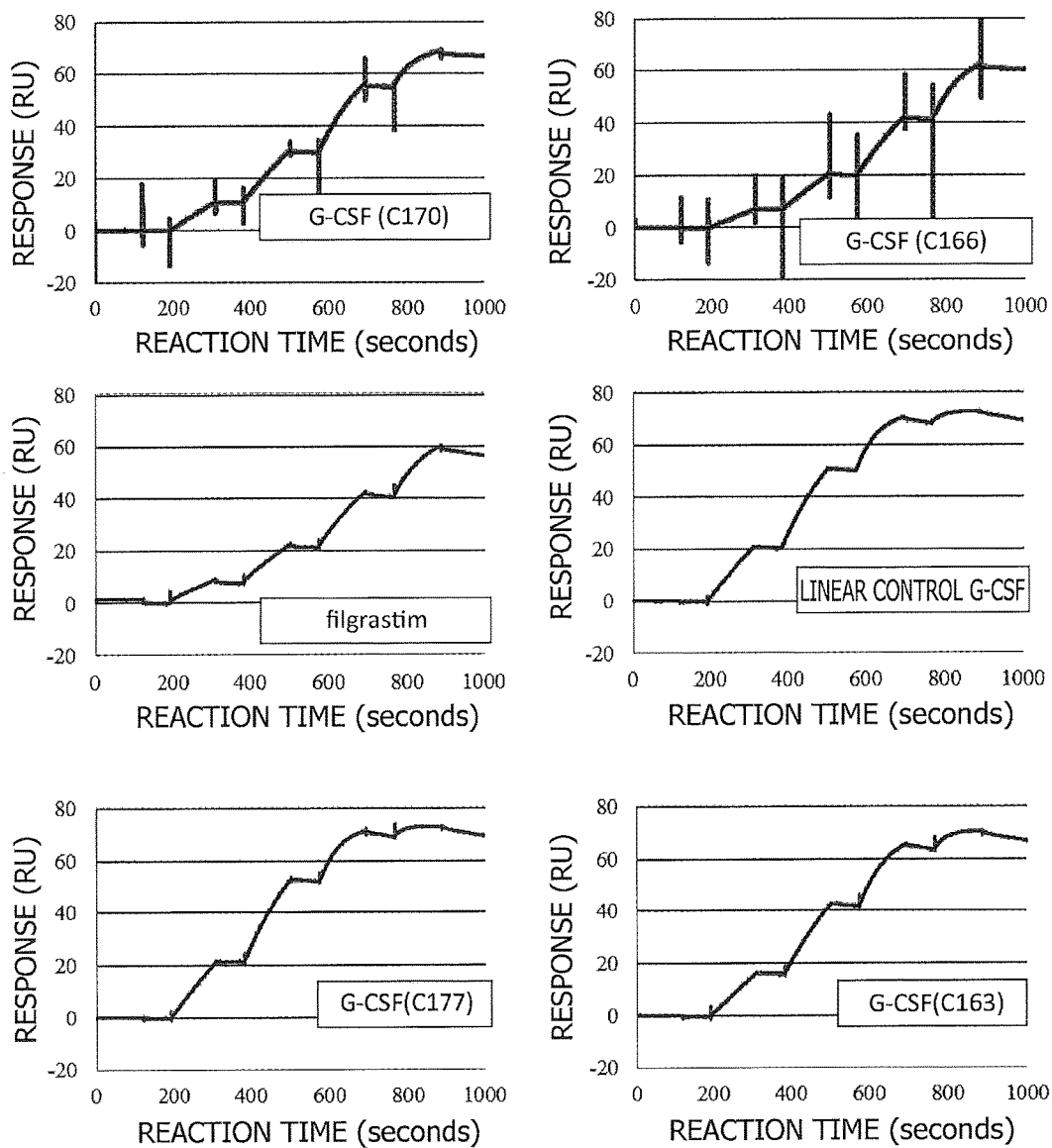

[Figure 11]
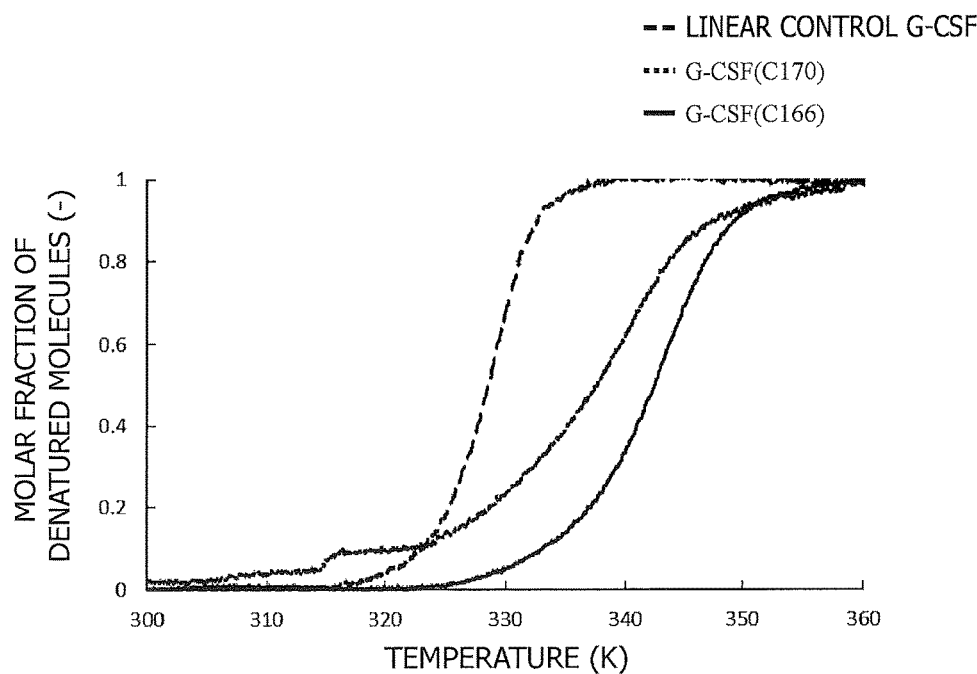
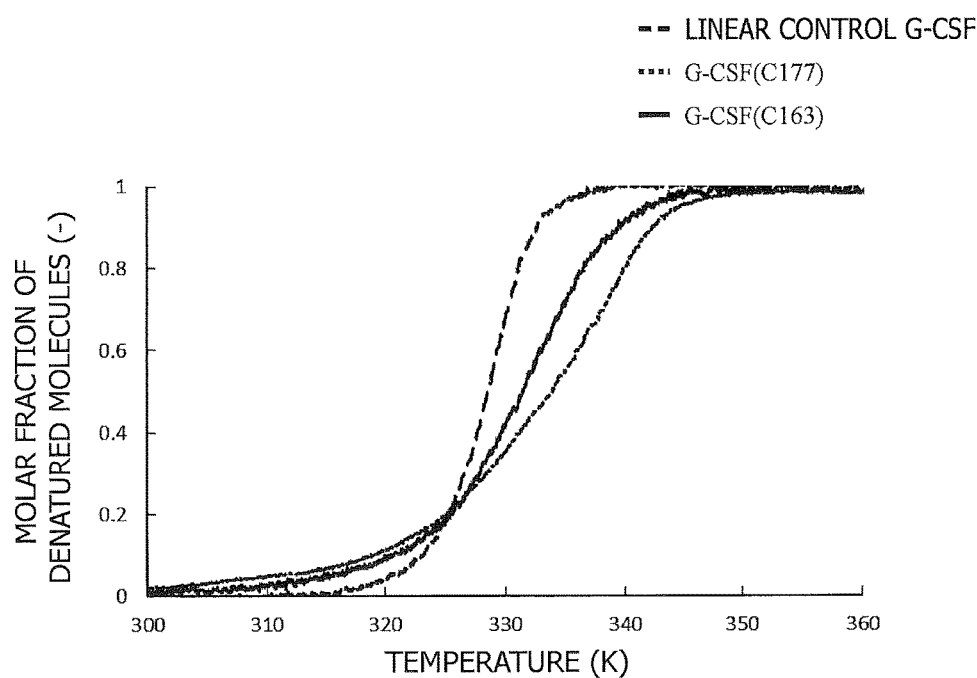

[Figure 12]
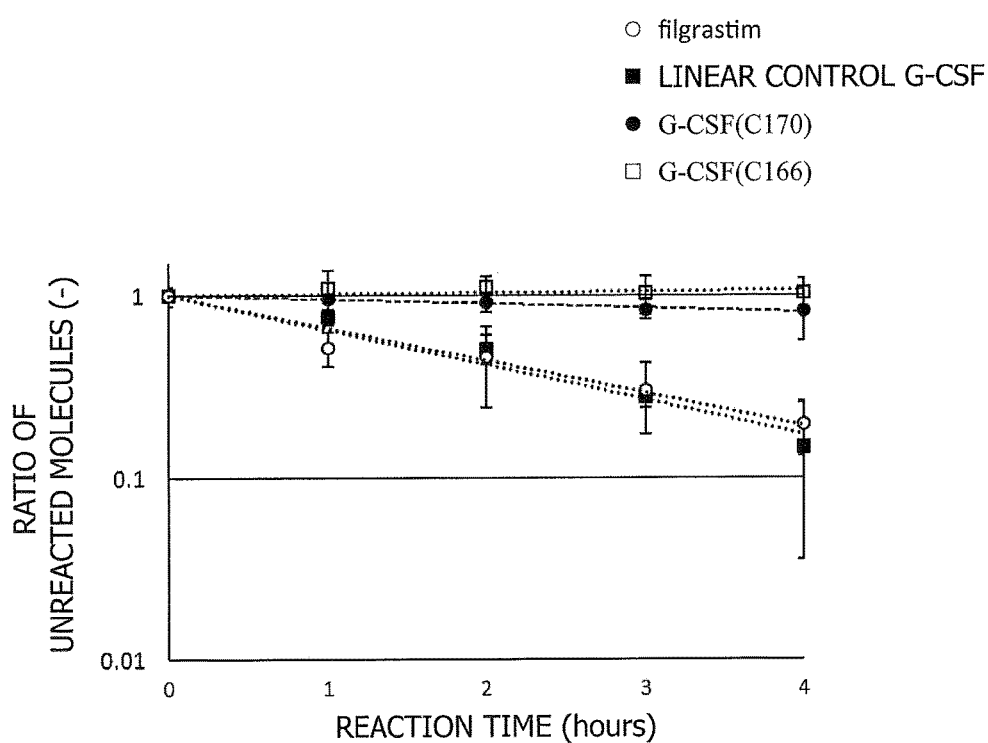

SEQUENCE LISTING

```
<160> NUMBER OF SEQ ID NOS: 36

<210> SEQ ID NO 1
<211> LENGTH: 175
<212> TYPE: PRT
<213> ORGANISM: artificial
<220> FEATURE:
<223> OTHER INFORMATION: G-CSF added M at N terminal and replaced
      residues 2 and 18 to A and S

<400> SEQUENCE: 1

Met Ala Pro Leu Gly Pro Ala Ser Ser Leu Pro Gln Ser Phe Leu Leu
1               5                   10                  15
```

```
Lys Ser Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
            35                  40                  45

Val Leu Leu Gly His Ser Leu Gly Ile Pro Trp Ala Pro Leu Ser Ser
        50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
            115                 120                 125

Pro Ala Leu Gln Pro Thr Gln Gly Ala Met Pro Ala Phe Ala Ser Ala
            130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175
```

<210> SEQ ID NO 2
<211> LENGTH: 177
<212> TYPE: PRT
<213> ORGANISM: artificial
<220> FEATURE:
<223> OTHER INFORMATION: G-CSF modified for cyclization

<400> SEQUENCE: 2

```
Ser Met Ala Pro Leu Gly Pro Ala Ser Ser Leu Pro Gln Ser Phe Leu
1               5                   10                  15

Leu Lys Ser Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
            35                  40                  45

Leu Val Leu Leu Gly His Ser Leu Gly Ile Pro Trp Ala Pro Leu Ser
        50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
            115                 120                 125

Ala Pro Ala Leu Gln Pro Thr Gln Gly Ala Met Pro Ala Phe Ala Ser
            130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Gly
```

<210> SEQ ID NO 3
<211> LENGTH: 170
<212> TYPE: PRT

```
<213> ORGANISM: artificial
<220> FEATURE:
<223> OTHER INFORMATION: G-CSF modified for cyclization

<400> SEQUENCE: 3

Ser Gly Pro Ala Ser Ser Leu Pro Gln Ser Phe Leu Leu Lys Ser Leu
1               5                   10                  15

Glu Gln Val Arg Lys Ile Gln Gly Asp Gly Ala Ala Leu Gln Glu Lys
            20                  25                  30

Leu Cys Ala Thr Tyr Lys Leu Cys His Pro Glu Glu Leu Val Leu Leu
        35                  40                  45

Gly His Ser Leu Gly Ile Pro Trp Ala Pro Leu Ser Ser Cys Pro Ser
    50                  55                  60

Gln Ala Leu Gln Leu Ala Gly Cys Leu Ser Gln Leu His Ser Gly Leu
65                  70                  75                  80

Phe Leu Tyr Gln Gly Leu Leu Gln Ala Leu Glu Gly Ile Ser Pro Glu
                85                  90                  95

Leu Gly Pro Thr Leu Asp Thr Leu Gln Leu Asp Val Ala Asp Phe Ala
            100                 105                 110

Thr Thr Ile Trp Gln Gln Met Glu Glu Leu Gly Met Ala Pro Ala Leu
        115                 120                 125

Gln Pro Thr Gln Gly Ala Met Pro Ala Phe Ala Ser Ala Phe Gln Arg
    130                 135                 140

Arg Ala Gly Gly Val Leu Val Ala Ser His Leu Gln Ser Phe Leu Glu
145                 150                 155                 160

Val Ser Tyr Arg Val Leu Arg His Leu Gly
                165                 170

<210> SEQ ID NO 4
<211> LENGTH: 166
<212> TYPE: PRT
<213> ORGANISM: artificial
<220> FEATURE:
<223> OTHER INFORMATION: G-CSF modified for cyclization

<400> SEQUENCE: 4

Ser Ser Leu Pro Gln Ser Phe Leu Leu Lys Ser Leu Glu Gln Val Arg
1               5                   10                  15

Lys Ile Gln Gly Asp Gly Ala

Val Leu Arg His Leu Gly
            165

<210> SEQ ID NO 5
<211> LENGTH: 163
<212> TYPE: PRT
<213> ORGANISM: artificial
<220> FEATURE:
<223> OTHER INFORMATION: G-CSF modified for cyclization

<400> SEQUENCE: 5

Ser Gln Ser Phe Leu Leu Lys Ser Leu Glu Gln Val Arg Lys Ile Gln
1               5                   10                  15

Gly Asp Gly Ala Ala Leu Gln Glu Lys Leu Cys Ala Thr Tyr Lys Leu
            20                  25                  30

Cys His Pro Glu Glu Leu Val Leu Leu Gly His Ser Leu Gly Ile Pro
        35                  40                  45

Trp Ala Pro Leu Ser Ser Cys Pro Ser Gln Ala Leu Gln Leu Ala Gly
    50                  55                  60

Cys Leu Ser Gln Leu His Ser Gly Leu Phe Leu Tyr Gln Gly Leu Leu
65                  70                  75                  80

Gln Ala Leu Glu Gly Ile Ser Pro Glu Leu Gly Pro Thr Leu Asp Thr
                85                  90                  95

Leu Gln Leu Asp Val Ala Asp Phe Ala Thr Thr Ile Trp Gln Gln Met
            100                 105                 110

Glu Glu Leu Gly Met Ala Pro Ala Leu Gln Pro Thr Gln Gly Ala Met
        115                 120                 125

Pro Ala Phe Ala Ser Ala Phe Gln Arg Arg Ala Gly Gly Val Leu Val
    130                 135                 140

Ala Ser His Leu Gln Ser Phe Leu Glu Val Ser Tyr Arg Val Leu Arg
145                 150                 155                 160

His Leu Gly

<210> SEQ ID NO 6
<211> LENGTH: 177
<212> TYPE: PRT
<213> ORGANISM: artificial
<220> FEATURE:
<223> OTHER INFORMATION: modified G-CSF cyclized by peptide bond
      formation between N and C terminals

<400> SEQUENCE: 6

Ser Met Ala Pro Leu Gly Pro Ala Ser Ser Leu Pro Gln Ser Phe Leu
1               5                   10                  15

Leu Lys Ser Leu Glu Gln Val Arg Lys Ile Gln Gly Asp Gly Ala Ala
            20                  25                  30

Leu Gln Glu Lys Leu Cys Ala Thr Tyr Lys Leu Cys His Pro Glu Glu
        35                  40                  45

Leu Val Leu Leu Gly His Ser Leu Gly Ile Pro Trp Ala Pro Leu Ser
    50                  55                  60

Ser Cys Pro Ser Gln Ala Leu Gln Leu Ala Gly Cys Leu Ser Gln Leu
65                  70                  75                  80

His Ser Gly Leu Phe Leu Tyr Gln Gly Leu Leu Gln Ala Leu Glu Gly
                85                  90                  95

Ile Ser Pro Glu Leu Gly Pro Thr Leu Asp Thr Leu Gln Leu Asp Val
            100                 105                 110

Ala Asp Phe Ala Thr Thr Ile Trp Gln Gln Met Glu Glu Leu Gly Met
        115                 120                 125

```
Ala Pro Ala Leu Gln Pro Thr Gln Gly Ala Met Pro Ala Phe Ala Ser
        130                 135                 140

Ala Phe Gln Arg Arg Ala Gly Gly Val Leu Val Ala Ser His Leu Gln
145                 150                 155                 160

Ser Phe Leu Glu Val Ser Tyr Arg Val Leu Arg His Leu Ala Gln Pro
                165                 170                 175

Gly

<210> SEQ ID NO 7
<211> LENGTH: 170
<212> TYPE: PRT
<213> ORGANISM: artificial
<220> FEATURE:
<223> OTHER INFORMATION: modified G-CSF cyclized by peptide bond
      formation between N and C terminals

<400> SEQUENCE: 7

Ser Gly Pro Ala Ser Ser Leu Pro Gln Ser Phe Leu Leu Lys Ser Leu
1               5                   10                  15

Glu Gln Val Arg Lys Ile Gln Gly Asp Gly Ala Ala Leu Gln Glu Lys
            20                  25                  30

Leu Cys Ala Thr Tyr Lys Leu Cys His Pro Glu Glu Leu Val Leu Leu
        35                  40                  45

Gly His Ser Leu Gly Ile Pro Trp Ala Pro Leu Ser Ser Cys Pro Ser
    50                  55                  60

Gln Ala Leu Gln Leu Ala Gly Cys Leu Ser Gln Leu His Ser Gly Leu
65                  70                  75                  80

Phe Leu Tyr Gln Gly Leu Leu Gln Ala Leu Glu Gly Ile Ser Pro Glu
                85                  90                  95

Leu Gly Pro Thr Leu Asp Thr Leu Gln Leu Asp Val Ala Asp Phe Ala
            100                 105                 110

Thr Thr Ile Trp Gln Gln Met Glu Glu Leu Gly Met Ala Pro Ala Leu
        115                 120                 125

Gln Pro Thr Gln Gly Ala Met Pro Ala Phe Ala Ser Ala Phe Gln Arg
    130                 135                 140

Arg Ala Gly Gly Val Leu Val Ala Ser His Leu Gln Ser Phe Leu Glu
145                 150                 155                 160

Val Ser Tyr Arg Val Leu Arg His Leu Gly
                165                 170

<210> SEQ ID NO 8
<211> LENGTH: 166
<212> TYPE: PRT
<213> ORGANISM: artificial
<220> FEATURE:
<223> OTHER INFORMATION: modified G-CSF cyclized by peptide bond
      formation between N and C terminals

<400> SEQUENCE: 8

Ser Ser Leu Pro Gln Ser Phe Leu Leu Lys Ser Leu Glu Gln Val Arg
1               5                   10                  15

Lys Ile Gln Gly Asp Gly Ala Ala Leu Gln Glu Lys Leu Cys Ala Thr
            20                  25                  30

Tyr Lys Leu Cys His Pro Glu Glu Leu Val Leu Leu Gly His Ser Leu
        35                  40                  45

Gly Ile Pro Trp Ala Pro Leu Ser Ser Cys Pro Ser Gln Ala Leu Gln
    50                  55                  60
```

```
Leu Ala Gly Cys Leu Ser Gln Leu His Ser Gly Leu Phe Leu Tyr Gln
 65                  70                  75                  80

Gly Leu Leu Gln Ala Leu Glu Gly Ile Ser Pro Glu Leu Gly Pro Thr
                 85                  90                  95

Leu Asp Thr Leu Gln Leu Asp Val Ala Asp Phe Ala Thr Thr Ile Trp
            100                 105                 110

Gln Gln Met Glu Glu Leu Gly Met Ala Pro Ala Leu Gln Pro Thr Gln
        115                 120                 125

Gly Ala Met Pro Ala Phe Ala Ser Ala Phe Gln Arg Arg Ala Gly Gly
    130                 135                 140

Val Leu Val Ala Ser His Leu Gln Ser Phe Leu Glu Val Ser Tyr Arg
145                 150                 155                 160

Val Leu Arg His Leu Gly
                165

<210> SEQ ID NO 9
<211> LENGTH: 163
<212> TYPE: PRT
<213> ORGANISM: artificial
<220> FEATURE:
<223> OTHER INFORMATION: modiefied G-CSF cyclized by peptide bond
      formation between N and C terminals

<400> SEQUENCE: 9

Ser Gln Ser Phe Leu Leu Lys Ser Leu Glu Gln Val Arg Lys Ile Gln
 1               5                  10                  15

Gly Asp Gly Ala Ala Leu Gln Glu Lys Leu Cys Ala Thr Tyr Lys Leu
                 20                  25                  30

Cys His Pro Glu Glu Leu Val Leu Leu Gly His Ser Leu Gly Ile Pro
             35                  40                  45

Trp Ala Pro Leu Ser Ser Cys Pro Ser Gln Ala Leu Gln Leu Ala Gly
 50                  55                  60

Cys Leu Ser Gln Leu His Ser Gly Leu Phe Leu Tyr Gln Gly Leu Leu
 65                  70                  75                  80

Gln Ala Leu Glu Gly Ile Ser Pro Glu Leu Gly Pro Thr Leu Asp Thr
                 85                  90                  95

Leu Gln Leu Asp Val Ala Asp Phe Ala Thr Thr Ile Trp Gln Gln Met
            100                 105                 110

Glu Glu Leu Gly Met Ala Pro Ala Leu Gln Pro Thr Gln Gly Ala Met
        115                 120                 125

Pro Ala Phe Ala Ser Ala Phe Gln Arg Arg Ala Gly Gly Val Leu Val
    130                 135                 140

Ala Ser His Leu Gln Ser Phe Leu Glu Val Ser Tyr Arg Val Leu Arg
145                 150                 155                 160

His Leu Gly

<210> SEQ ID NO 10
<211> LENGTH: 325
<212> TYPE: PRT
<213> ORGANISM: artificial
<220> FEATURE:
<223> OTHER INFORMATION: modified G-CSF fused with DnaE-C and DnaE-N

<400> SEQUENCE: 10

Met Val Lys Ile Ala Thr Arg Lys Tyr Leu Gly Lys Gln Asn Val Tyr
 1               5                  10                  15

Asp Ile Gly Val Glu Arg Asp His Asn Phe Ala Leu Lys Asn Gly Phe
                 20                  25                  30
```

Ile Ala Ser Asn Ser Met Ala Pro Leu Gly Pro Ala Ser Ser Leu Pro
             35                  40                  45

Gln Ser Phe Leu Leu Lys Ser Leu Glu Gln Val Arg Lys Ile Gln Gly
     50                  55                  60

Asp Gly Ala Ala Leu Gln Glu Lys Leu Cys Ala Thr Tyr Lys Leu Cys
 65                  70                  75                  80

His Pro Glu Glu Leu Val Leu Leu Gly His Ser Leu Gly Ile Pro Trp
                 85                  90                  95

Ala Pro Leu Ser Ser Cys Pro Ser Gln Ala Leu Gln Leu Ala Gly Cys
                100                 105                 110

Leu Ser Gln Leu His Ser Gly Leu Phe Leu Tyr Gln Gly Leu Leu Gln
            115                 120                 125

Ala Leu Glu Gly Ile Ser Pro Glu Leu Gly Pro Thr Leu Asp Thr Leu
        130                 135                 140

Gln Leu Asp Val Ala Asp Phe Ala Thr Thr Ile Trp Gln Gln Met Glu
145                 150                 155                 160

Glu Leu Gly Met Ala Pro Ala Leu Gln Pro Thr Gln Gly Ala Met Pro
                165                 170                 175

Ala Phe Ala Ser Ala Phe Gln Arg Arg Ala Gly Gly Val Leu Val Ala
            180                 185                 190

Ser His Leu Gln Ser Phe Leu Glu Val Ser Tyr Arg Val Leu Arg His
        195                 200                 205

Leu Ala Gln Pro Gly Cys Leu Ser Tyr Glu Thr Glu Ile Leu Thr Val
    210                 215                 220

Glu Tyr Gly Leu Leu Pro Ile Gly Lys Ile Val Glu Lys Arg Ile Glu
225                 230                 235                 240

Cys Thr Val Tyr Ser Val Asp Asn Asn Gly Asn Ile Tyr Thr Gln Pro
                245                 250                 255

Val Ala Gln Trp His Asp Arg Gly Glu Gln Glu Val Phe Glu Tyr Cys
            260                 265                 270

Leu Glu Asp Gly Ser Leu Ile Arg Ala Thr Lys Asp His Lys Phe Met
        275                 280                 285

Thr Val Asp Gly Gln Met Leu Pro Ile Asp Glu Ile Phe Glu Arg Glu
    290                 295                 300

Leu Asp Leu Met Arg Val Asp Asn Leu Pro Asn Ser Gly Ser Gly His
305                 310                 315                 320

His His His His His
            325

<210> SEQ ID NO 11
<211> LENGTH: 318
<212> TYPE: PRT
<213> ORGANISM: artificial
<220> FEATURE:
<223> OTHER INFORMATION: modified G-CSF fused with DnaE-C and DnaE-N

<400> SEQUENCE: 11

Met Val Lys Ile Ala Thr Arg Lys Tyr Leu Gly Lys Gln Asn Val Tyr
 1               5                  10                  15

Asp Ile Gly Val Glu Arg Asp His Asn Phe Ala Leu Lys Asn Gly Phe
                20                  25                  30

Ile Ala Ser Asn Ser Gly Pro Ala Ser Ser Leu Pro Gln Ser Phe Leu
            35                  40                  45

Leu Lys Ser Leu Glu Gln Val Arg Lys Ile Gln Gly Asp Gly Ala Ala
        50                  55                  60

Leu Gln Glu Lys Leu Cys Ala Thr Tyr Lys Leu Cys His Pro Glu Glu
65                  70                  75                  80

Leu Val Leu Leu Gly His Ser Leu Gly Ile Pro Trp Ala Pro Leu Ser
                85                  90                  95

Ser Cys Pro Ser Gln Ala Leu Gln Leu Ala Gly Cys Leu Ser Gln Leu
            100                 105                 110

His Ser Gly Leu Phe Leu Tyr Gln Gly Leu Leu Gln Ala Leu Glu Gly
        115                 120                 125

Ile Ser Pro Glu Leu Gly Pro Thr Leu Asp Thr Leu Gln Leu Asp Val
    130                 135                 140

Ala Asp Phe Ala Thr Thr Ile Trp Gln Gln Met Glu Glu Leu Gly Met
145                 150                 155                 160

Ala Pro Ala Leu Gln Pro Thr Gln Gly Ala Met Pro Ala Phe Ala Ser
                165                 170                 175

Ala Phe Gln Arg Arg Ala Gly Gly Val Leu Val Ala Ser His Leu Gln
            180                 185                 190

Ser Phe Leu Glu Val Ser Tyr Arg Val Leu Arg His Leu Gly Cys Leu
        195                 200                 205

Ser Tyr Glu Thr Glu Ile Leu Thr Val Glu Tyr Gly Leu Leu Pro Ile
    210                 215                 220

Gly Lys Ile Val Glu Lys Arg Ile Glu Cys Thr Val Tyr Ser Val Asp
225                 230                 235                 240

Asn Asn Gly Asn Ile Tyr Thr Gln Pro Val Ala Gln Trp His Asp Arg
                245                 250                 255

Gly Glu Gln Glu Val Phe Glu Tyr Cys Leu Glu Asp Gly Ser Leu Ile
            260                 265                 270

Arg Ala Thr Lys Asp His Lys Phe Met Thr Val Asp Gly Gln Met Leu
        275                 280                 285

Pro Ile Asp Glu Ile Phe Glu Arg Glu Leu Asp Leu Met Arg Val Asp
    290                 295                 300

Asn Leu Pro Asn Ser Gly Ser Gly His His His His His His
305                 310                 315

<210> SEQ ID NO 12
<211> LENGTH: 314
<212> TYPE: PRT
<213> ORGANISM: artificial
<220> FEATURE:
<223> OTHER INFORMATION: modified G-CSF fused with DnaE-C and DnaE-N

<400> SEQUENCE: 12

Met Val Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Ser Ser Leu Pro Gln Ser Phe Leu Leu Lys Ser Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

```
Phe Leu Tyr Gln Gly Leu Leu Gln Ala Leu Glu Gly Ile Ser Pro Glu
            115                 120                 125

Leu Gly Pro Thr Leu Asp Thr Leu Gln Leu Asp Val Ala Asp Phe Ala
130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Gly Cys Leu Ser Tyr Glu Thr
        195                 200                 205

Glu Ile Leu Thr Val Glu Tyr Gly Leu Leu Pro Ile Gly Lys Ile Val
    210                 215                 220

Glu Lys Arg Ile Glu Cys Thr Val Tyr Ser Val Asp Asn Asn Gly Asn
225                 230                 235                 240

Ile Tyr Thr Gln Pro Val Ala Gln Trp His Asp Arg Gly Glu Gln Glu
                245                 250                 255

Val Phe Glu Tyr Cys Leu Glu Asp Gly Ser Leu Ile Arg Ala Thr Lys
            260                 265                 270

Asp His Lys Phe Met Thr Val Asp Gly Gln Met Leu Pro Ile Asp Glu
        275                 280                 285

Ile Phe Glu Arg Glu Leu Asp Leu Met Arg Val Asp Asn Leu Pro Asn
    290                 295                 300

Ser Gly Ser Gly His His His His His His
305                 310

<210> SEQ ID NO 13
<211> LENGTH: 311
<212> TYPE: PRT
<213> ORGANISM: artificial
<220> FEATURE:
<223> OTHER INFORMATION: modified G-CSF fused with DnaE-C and DnaE-N

<400> SEQUENCE: 13

Met Val Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn Ser Gln Ser Phe Leu Leu Lys Ser Leu Glu Gln Val
        35                  40                  45

Arg Lys Ile Gln Gly Asp Gly Ala Ala Leu Gln Glu Lys Leu Cys Ala
    50                  55                  60

Thr Tyr Lys Leu Cys His Pro Glu Glu Leu Val Leu Leu Gly His Ser
65                  70                  75                  80

Leu Gly Ile Pro Trp Ala Pro Leu Ser Ser Cys Pro Ser Gln Ala Leu
                85                  90                  95

Gln Leu Ala Gly Cys Leu Ser Gln Leu His Ser Gly Leu Phe Leu Tyr
            100                 105                 110

Gln Gly Leu Leu Gln Ala Leu Glu Gly Ile Ser Pro Glu Leu Gly Pro
        115                 120                 125

Thr Leu Asp Thr Leu Gln Leu Asp Val Ala Asp Phe Ala Thr Thr Ile
    130                 135                 140

Trp Gln Gln Met Glu Glu Leu Gly Met Ala Pro Ala Leu Gln Pro Thr
145                 150                 155                 160
```

```
Gln Gly Ala Met Pro Ala Phe Ala Ser Ala Phe Gln Arg Arg Ala Gly
                165                 170                 175

Gly Val Leu Val Ala Ser His Leu Gln Ser Phe Leu Glu Val Ser Tyr
            180                 185                 190

Arg Val Leu Arg His Leu Gly Cys Leu Ser Tyr Glu Thr Glu Ile Leu
            195                 200                 205

Thr Val Glu Tyr Gly Leu Leu Pro Ile Gly Lys Ile Val Glu Lys Arg
        210                 215                 220

Ile Glu Cys Thr Val Tyr Ser Val Asp Asn Asn Gly Asn Ile Tyr Thr
225                 230                 235                 240

Gln Pro Val Ala Gln Trp His Asp Arg Gly Glu Gln Glu Val Phe Glu
                245                 250                 255

Tyr Cys Leu Glu Asp Gly Ser Leu Ile Arg Ala Thr Lys Asp His Lys
            260                 265                 270

Phe Met Thr Val Asp Gly Gln Met Leu Pro Ile Asp Glu Ile Phe Glu
        275                 280                 285

Arg Glu Leu Asp Leu Met Arg Val Asp Asn Leu Pro Asn Ser Gly Ser
            290                 295                 300

Gly His His His His His
305                 310

<210> SEQ ID NO 14
<211> LENGTH: 175
<212> TYPE: PRT
<213> ORGANISM: artificial
<220> FEATURE:
<223> OTHER INFORMATION: G-CSF added M at N terminal

<400> SEQUENCE: 14

Met Thr Pro Leu Gly Pro Ala Ser Ser Leu Pro Gln Ser Phe Leu Leu
1               5                   10                  15

Lys Cys Leu Glu Gln Val Arg Lys Ile Gln Gly Asp Gly Ala Ala Leu
            20                  25                  30

Gln Glu Lys Leu Cys Ala Thr Tyr Lys Leu Cys His Pro Glu Glu Leu
        35                  40                  45

Val Leu Leu Gly His Ser Leu Gly Ile Pro Trp Ala Pro Leu Ser Ser
    50                  55                  60

Cys Pro Ser Gln Ala Leu Gln Leu Ala Gly Cys Leu Ser Gln Leu His
65                  70                  75                  80

Ser Gly Leu Phe Leu Tyr Gln Gly Leu Leu Gln Ala Leu Glu Gly Ile
                85                  90                  95

Ser Pro Glu Leu Gly Pro Thr Leu Asp Thr Leu Gln Leu Asp Val Ala
            100                 105                 110

Asp Phe Ala Thr Thr Ile Trp Gln Gln Met Glu Glu Leu Gly Met Ala
        115                 120                 125

Pro Ala Leu Gln Pro Thr Gln Gly Ala Met Pro Ala Phe Ala Ser Ala
    130                 135                 140

Phe Gln Arg Arg Ala Gly Gly Val Leu Val Ala Ser His Leu Gln Ser
145                 150                 155                 160

Phe Leu Glu Val Ser Tyr Arg Val Leu Arg His Leu Ala Gln Pro
                165                 170                 175

<210> SEQ ID NO 15
<211> LENGTH: 36
<212> TYPE: PRT
<213> ORGANISM: artificial
```

<220> FEATURE:
<223> OTHER INFORMATION: DnaE-C

<400> SEQUENCE: 15

Met Val Lys Ile Ala Thr Arg Lys Tyr Leu Gly Lys Gln Asn Val Tyr
1               5                   10                  15

Asp Ile Gly Val Glu Arg Asp His Asn Phe Ala Leu Lys Asn Gly Phe
            20                  25                  30

Ile Ala Ser Asn
        35

<210> SEQ ID NO 16
<211> LENGTH: 112
<212> TYPE: PRT
<213> ORGANISM: artificial
<220> FEATURE:
<223> OTHER INFORMATION: DnaE-N

<400> SEQUENCE: 16

Cys Leu Ser Tyr Glu Thr Glu Ile Leu Thr Val Glu Tyr Gly Leu Leu
1               5                   10                  15

Pro Ile Gly Lys Ile Val Glu Lys Arg Ile Glu Cys Thr Val Tyr Ser
            20                  25                  30

Val Asp Asn Asn Gly Asn Ile Tyr Thr Gln Pro Val Ala Gln Trp His
        35                  40                  45

Asp Arg Gly Glu Gln Glu Val Phe Glu Tyr Cys Leu Glu Asp Gly Ser
    50                  55                  60

Leu Ile Arg Ala Thr Lys Asp His Lys Phe Met Thr Val Asp Gly Gln
65                  70                  75                  80

Met Leu Pro Ile Asp Glu Ile Phe Glu Arg Glu Leu Asp Leu Met Arg
                85                  90                  95

Val Asp Asn Leu Pro Asn Ser Gly Ser Gly His His His His His His
            100                 105                 110

<210> SEQ ID NO 17
<211> LENGTH: 531
<212> TYPE: DNA
<213> ORGANISM: artificial
<220> FEATURE:
<223> OTHER INFORMATION: G-CSF modified for cyclization

<400> SEQUENCE: 17
agcatggcac cattaggtcc agcgagcagc ctgccgcaga gctttctgct gaaaagcctg      60
gaacaggtgc gtaaaattca gggtgatggt gcggcgctgc aagaaaaact gtgcgcgacc    120
tataaactgt gccatccgga agagctggtg ctgctgggcc atagcctggg tattccgtgg    180
gcaccgctgt ctagctgtcc gagccaggcg ctgcaactgg ccggttgtct gagccagctg    240
catagcggcc tgtttctgta tcagggcctg ctgcaagcgc tggaaggcat tagcccggag    300
ctgggcccga ctctggatac cctgcaactg gatgtggcgg attttgcgac caccatttgg    360
cagcagatgg aagagctggg catggcaccg gcgctgcaac cgacccaggg tgccatgccg    420
gcgtttgcga gcgcgtttca gcgtcgtgcg ggcggtgttc tggtggcgag ccatctgcaa    480
tcttttctgg aagtgagcta tcgtgtgctg cgtcatctgg cccagccggg c             531

<210> SEQ ID NO 18
<211> LENGTH: 510
<212> TYPE: DNA
<213> ORGANISM: artificial
<220> FEATURE:

<223> OTHER INFORMATION: G-CSF modified for cyclization

<400> SEQUENCE: 18

| | | | | | |
|---|---|---|---|---|---|
| agcggtccag | cgagcagcct | gccgcagagc | tttctgctga | aaagcctgga | acaggtgcgt | 60 |
| aaaattcagg | gtgatggtgc | ggcgctgcaa | gaaaaactgt | gcgcgaccta | taaactgtgc | 120 |
| catccggaag | agctggtgct | gctgggccat | agcctgggta | ttccgtgggc | accgctgtct | 180 |
| agctgtccga | ccaggcgct | gcaactggcc | ggttgtctga | gccagctgca | tagcggcctg | 240 |
| tttctgtatc | agggcctgct | gcaagcgctg | gaaggcatta | gcccggagct | gggcccgact | 300 |
| ctggataccc | tgcaactgga | tgtggcggat | tttgcgacca | ccatttggca | gcagatggaa | 360 |
| gagctgggca | tggcaccggc | gctgcaaccg | acccagggtg | ccatgccggc | gtttgcgagc | 420 |
| gcgtttcagc | gtcgtgcggg | cggtgttctg | gtggcgagcc | atctgcaatc | ttttctggaa | 480 |
| gtgagctatc | gtgtgctgcg | tcatctgggc | | | | 510 |

<210> SEQ ID NO 19
<211> LENGTH: 498
<212> TYPE: DNA
<213> ORGANISM: artificial
<220> FEATURE:
<223> OTHER INFORMATION: G-CSF modified for cyclization

<400> SEQUENCE: 19

| | | | | | |
|---|---|---|---|---|---|
| agcagcctgc | cgcagagctt | tctgctgaaa | agcctggaac | aggtgcgtaa | aattcagggt | 60 |
| gatggtgcgg | cgctgcaaga | aaaactgtgc | gcgacctata | aactgtgcca | tccggaagag | 120 |
| ctggtgctgc | tgggccatag | cctgggtatt | ccgtgggcac | cgctgtctag | ctgtccgagc | 180 |
| caggcgctgc | aactggccgg | ttgtctgagc | cagctgcata | gcggcctgtt | tctgtatcag | 240 |
| ggcctgctgc | aagcgctgga | aggcattagc | ccggagctgg | gcccgactct | ggataccctg | 300 |
| caactggatg | tggcggattt | tgcgaccacc | atttggcagc | agatggaaga | gctgggcatg | 360 |
| gcaccggcgc | tgcaaccgac | ccagggtgcc | atgccggcgt | ttgcgagcgc | gtttcagcgt | 420 |
| cgtgcgggcg | gtgttctggt | ggcgagccat | ctgcaatctt | ttctggaagt | gagctatcgt | 480 |
| gtgctgcgtc | atctgggc | | | | | 498 |

<210> SEQ ID NO 20
<211> LENGTH: 489
<212> TYPE: DNA
<213> ORGANISM: artificial
<220> FEATURE:
<223> OTHER INFORMATION: G-CSF modified for cyclization

<400> SEQUENCE: 20

| | | | | | |
|---|---|---|---|---|---|
| agccagagct | ttctgctgaa | aagcctggaa | caggtgcgta | aaattcaggg | tgatggtgcg | 60 |
| gcgctgcaag | aaaaactgtg | cgcgacctat | aaactgtgcc | atccggaaga | gctggtgctg | 120 |
| ctgggccata | gcctgggtat | tccgtgggca | ccgctgtcta | gctgtccgag | ccaggcgctg | 180 |
| caactggccg | gttgtctgag | ccagctgcat | agcggcctgt | ttctgtatca | gggcctgctg | 240 |
| caagcgctgg | aaggcattag | cccggagctg | ggcccgactc | tggataccct | gcaactggat | 300 |
| gtggcggatt | ttgcgaccac | catttggcag | cagatggaag | agctgggcat | ggcaccggcg | 360 |
| ctgcaaccga | cccagggtgc | catgccggcg | tttgcgagcg | cgtttcagcg | tcgtgcgggc | 420 |
| ggtgttctgg | tggcgagcca | tctgcaatct | tttctggaag | tgagctatcg | tgtgctgcgt | 480 |
| catctgggc | | | | | | 489 |

<210> SEQ ID NO 21
<211> LENGTH: 978
<212> TYPE: DNA
<213> ORGANISM: artificial
<220> FEATURE:
<223> OTHER INFORMATION: modified G-CSF fused with DnaE-C and DnaE-N

<400> SEQUENCE: 21

| | | | | | |
|---|---|---|---|---|---|
| atggtgaaaa | tagccacacg | caaatatctg | ggcaaacaga | acgtgtatga | tattggcgtg | 60 |
| gaacgcgatc | ataactttgc | gctgaaaaac | ggcttcatag | ctagcaatag | catggcacca | 120 |
| ttaggtccag | cgagcagcct | gccgcagagc | tttctgctga | aaagcctgga | acaggtgcgt | 180 |
| aaaattcagg | gtgatggtgc | ggcgctgcaa | gaaaaactgt | gcgcgaccta | taaactgtgc | 240 |
| catccggaag | agctggtgct | gctgggccat | agcctgggta | ttccgtgggc | accgctgtct | 300 |
| agctgtccga | gccaggcgct | gcaactggcc | ggttgtctga | gccagctgca | tagcggcctg | 360 |
| tttctgtatc | agggcctgct | gcaagcgctg | gaaggcatta | gcccggagct | gggcccgact | 420 |
| ctggataccc | tgcaactgga | tgtggcggat | tttgcgacca | ccatttggca | gcagatggaa | 480 |
| gagctgggca | tggcaccggc | gctgcaaccg | acccagggtg | ccatgccggc | gtttgcgagc | 540 |
| gcgtttcagc | gtcgtgcggg | cggtgttctg | gtggcgagcc | atctgcaatc | ttttctggaa | 600 |
| gtgagctatc | gtgtgctgcg | tcatctggcc | cagccgggct | gtttatcata | tgaaacggaa | 660 |
| atattgaccg | tggaatatgg | cctgctgccg | attggcaaaa | ttgtgaaaaa | acgcattgaa | 720 |
| tgcaccgtgt | atagcgtgga | taacaacggc | aacatttata | cccagccggt | ggcgcagtgg | 780 |
| catgatcgcg | gcgaacagga | agtgtttgaa | tattgcctgg | aagatggcag | cctgattcgc | 840 |
| gcgaccaaag | atcataaatt | tatgaccgtg | gatggccaga | tgctgccgat | tgatgaaatt | 900 |
| tttgaacgcg | aactggatct | gatgcgggtt | gataatttgc | gaatagcgg | cagcggccat | 960 |
| caccatcacc | atcactaa | | | | | 978 |

<210> SEQ ID NO 22
<211> LENGTH: 957
<212> TYPE: DNA
<213> ORGANISM: artificial
<220> FEATURE:
<223> OTHER INFORMATION: modified G-CSF fused with DnaE-C and DnaE-N

<400> SEQUENCE: 22

| | | | | | |
|---|---|---|---|---|---|
| atggtgaaaa | tagccacacg | caaatatctg | ggcaaacaga | acgtgtatga | tattggcgtg | 60 |
| gaacgcgatc | ataactttgc | gctgaaaaac | ggcttcatag | ctagcaatag | cggtccagcg | 120 |
| agcagcctgc | cgcagagctt | tctgctgaaa | agcctggaac | aggtgcgtaa | aattcagggt | 180 |
| gatggtgcgg | cgctgcaaga | aaaactgtgc | gcgacctata | aactgtgcca | tccggaagag | 240 |
| ctggtgctgc | tgggccatag | cctgggtatt | ccgtgggcac | cgctgtctag | ctgtccgagc | 300 |
| caggcgctgc | aactggccgg | ttgtctgagc | cagctgcata | gcggcctgtt | tctgtatcag | 360 |
| ggcctgctgc | aagcgctgga | aggcattagc | ccggagctgg | gcccgactct | ggatacctg | 420 |
| caactggatg | tggcggattt | tgcgaccacc | atttggcagc | agatggaaga | gctgggcatg | 480 |
| gcaccggcgc | tgcaaccgac | ccagggtgcc | atgccggcgt | ttgcgagcgc | gtttcagcgt | 540 |
| cgtgcgggcg | gtgttctggt | ggcgagccat | ctgcaatctt | ttctggaagt | gagctatcgt | 600 |
| gtgctgcgtc | atctgggctg | tttatcatat | gaaacggaaa | tattgaccgt | ggaatatggc | 660 |
| ctgctgccga | ttggcaaaat | tgtgaaaaaa | cgcattgaat | gcaccgtgta | tagcgtggat | 720 |
| aacaacggca | acatttatac | ccagccggtg | gcgcagtggc | atgatcgcgg | cgaacaggaa | 780 |

```
gtgtttgaat attgcctgga agatggcagc ctgattcgcg cgaccaaaga tcataaattt    840
atgaccgtgg atggccagat gctgccgatt gatgaaattt ttgaacgcga actggatctg    900
atgcgggttg ataatttgcc gaatagcggc agcggccatc accatcacca tcactaa      957
```

```
<210> SEQ ID NO 23
<211> LENGTH: 945
<212> TYPE: DNA
<213> ORGANISM: artificial
<220> FEATURE:
<223> OTHER INFORMATION: modified G-CSF fused with DnaE-C and DnaE-N

<400> SEQUENCE: 23
atggtgaaaa tagccacacg caaatatctg ggcaaacaga acgtgtatga tattggcgtg     60
gaacgcgatc ataactttgc gctgaaaaac ggcttcatag ctagcaatag cagcctgccg    120
cagagctttc tgctgaaaag cctggaacag gtgcgtaaaa ttcagggtga tggtgcggcg    180
ctgcaagaaa actgtgcgc gacctataaa ctgtgccatc cggaagagct ggtgctgctg    240
ggccatagcc tgggtattcc gtgggcaccg ctgtctagct gtccgagcca ggcgctgcaa    300
ctggccggtt gtctgagcca gctgcatagc ggcctgtttc tgtatcaggg cctgctgcaa    360
gcgctggaag cattagcccc ggagctgggc ccgactctgg atacctgca actggatgtg    420 gcggattttg cgaccaccat ttggcagcag atggaagagc tgggcatggc accggcgctg    480
caaccgaccc aggtgccat gccggcgttt gcgagcgcgt ttcagcgtcg tgcgggcggt    540
gttctggtgg cgagccatct gcaatctttt ctggaagtga gctatcgtgt gctgcgtcat    600
ctgggctgtt tatcatatga aacgaaaata ttgaccgtgg aatatggcct gctgccgatt    660
ggcaaaattg tggaaaaacg cattgaatgc accgtgtata gcgtggataa caacggcaac    720 atttatacccc agccggtggc gcagtggcat gatcgcggcg aacaggaagt gtttgaatat    780
tgcctggaag atggcagcct gattcgcgcg accaaagatc ataaatttat gaccgtggat    840
ggccagatgc tgccgattga tgaaattttt gaacgcgaac tggatctgat gcgggttgat    900
aatttgccga atagcggcag cggccatcac catcaccatc actaa                    945
```

```
<210> SEQ ID NO 24
<211> LENGTH: 936
<212> TYPE: DNA
<213> ORGANISM: artificial
<220> FEATURE:
<223> OTHER INFORMATION: modified G-CSF fused with DnaE-C and DnaE-N

<400> SEQUENCE: 24
atggtgaaaa tagccacacg caaatatctg ggcaaacaga acgtgtatga tattggcgtg     60
gaacgcgatc ataactttgc gctgaaaaac ggcttcatag ctagcaatag ccagagcttt    120
ctgctgaaaa gcctggaaca ggtgcgtaaa attcagggtg atggtgcggc gctgcaagaa    180
aaactgtgcg cgacctataa actgtgccat ccggaagagc tggtgctgct gggccatagc    240
ctgggtattc gtgggcacc gctgtctagc tgtccgagcc aggcgctgca actggccggt    300
tgtctgagcc agctgcatag cggcctgttt ctgtatcagg gcctgctgca agcgctggaa    360
ggcattagcc cggagctggg cccgactctg gatacctgc aactggatgt ggcggatttt    420
gcgaccacca tttggcagca gatggaagag ctgggcatgg caccggcgct gcaaccgacc    480
cagggtgcca tgccggcgtt tgcgagcgcg tttcagcgtc gtgcgggcgg tgttctggtg    540
gcgagccatc tgcaatcttt tctggaagtg agctatcgtg tgctgcgtca tctgggctgt    600
ttatcatatg aaacggaaat attgaccgtg gaatatggcc tgctgccgat tggcaaaatt    660
```

-continued

```
gtggaaaaac gcattgaatg caccgtgtat agcgtggata acaacggcaa catttatacc    720
cagccggtgg cgcagtggca tgatcgcggc gaacaggaag tgtttgaata ttgcctggaa    780
gatggcagcc tgattcgcgc gaccaaagat cataaattta tgaccgtgga tggccagatg    840
ctgccgattg atgaaatttt tgaacgcgaa ctggatctga tgcgggttga taatttgccg    900
aatagcggca gcggccatca ccatcaccat cactaa                              936
```

<210> SEQ ID NO 25
<211> LENGTH: 525
<212> TYPE: DNA
<213> ORGANISM: artificial
<220> FEATURE:
<223> OTHER INFORMATION: G-CSF added M at N terminal and replaced
      residues 2 and 18 to A and S

<400> SEQUENCE: 25

```
atggcaccat taggtccagc gagcagcctg ccgcagagct ttctgctgaa aagcctggaa    60
caggtgcgta aaattcaggg tgatggtgcg gcgctgcaag aaaaactgtg cgcgacctat   120
aaactgtgcc atccggaaga gctggtgctg ctgggccata gcctgggtat tccgtgggca   180
ccgctgtcta gctgtccgag ccaggcgctg caactggccg ttgtctgag ccagctgcat    240 agcggcctgt ttctgtatca gggcctgctg caagcgctgg aaggcattag cccggagctg   300
ggcccgactc tggatacccc gcaactggat gtggcggatt ttgcgaccac catttggcag   360
cagatggaag agctgggcat ggcaccggcg ctgcaaccga cccagggtgc catgccggcg   420
tttgcgagcg cgtttcagcg tcgtgcgggc ggtgttctgg tggcgagcca tctgcaatct   480
tttctggaag tgagctatcg tgtgctgcgt catctggccc agccg                   525
```

<210> SEQ ID NO 26
<211> LENGTH: 48
<212> TYPE: DNA
<213> ORGANISM: artificial
<220> FEATURE:
<223> OTHER INFORMATION: primer

<400> SEQUENCE: 26

```
tataccatgg caccattagg tccagcgagc agcctgccgc agagcttt                 48
```

<210> SEQ ID NO 27
<211> LENGTH: 25
<212> TYPE: DNA
<213> ORGANISM: artificial
<220> FEATURE:
<223> OTHER INFORMATION: primer

<400> SEQUENCE: 27

```
atggatcctt acggctgggc cagat                                          25
```

<210> SEQ ID NO 28
<211> LENGTH: 477
<212> TYPE: DNA
<213> ORGANISM: artificial
<220> FEATURE:
<223> OTHER INFORMATION: coding continuously DnaE-C and -N derived from
      Nostoc punctiforme

<400> SEQUENCE: 28

```
atggtgaaaa tagccacacg caaatatctg ggcaaacaga acgtgtatga tattggcgtg    60
gaacgcgatc ataactttgc gctgaaaaac ggcttcatag ctagcaattg ttttaacaaa   120
```

```
agccattttg cggaatattg tttatcatat gaaacggaaa tattgaccgt ggaatatggc      180
ctgctgccga ttggcaaaat tgtggaaaaa cgcattgaat gcaccgtgta tagcgtggat      240
aacaacggca acatttatac ccagccggtg gcgcagtggc atgatcgcgg cgaacaggaa      300
gtgtttgaat attgcctgga agatggcagc ctgattcgcg cgaccaaaga tcataaattt      360
atgaccgtgg atggccagat gctgccgatt gatgaaattt ttgaacgcga actggatctg      420
atgcgggttg ataatttgcc gaatagcggc agcggccatc accatcacca tcactaa       477
```

```
<210> SEQ ID NO 29
<211> LENGTH: 33
<212> TYPE: DNA
<213> ORGANISM: artificial
<220> FEATURE:
<223> OTHER INFORMATION: primer

<400> SEQUENCE: 29
aaagctagca atagcatggc accattaggt cca                                    33

<210> SEQ ID NO 30
<211> LENGTH: 38
<212> TYPE: DNA
<213> ORGANISM: artificial
<220> FEATURE:
<223> OTHER INFORMATION: primer

<400> SEQUENCE: 30
aaaaattcat atgataaaca gcccggctgg gccagatg                               38

<210> SEQ ID NO 31
<211> LENGTH: 30
<212> TYPE: DNA
<213> ORGANISM: artificial
<220> FEATURE:
<223> OTHER INFORMATION: primer

<400> SEQUENCE: 31
aaagctagca atagcggtcc agcgagcagc                                        30

<210> SEQ ID NO 32
<211> LENGTH: 41
<212> TYPE: DNA
<213> ORGANISM: artificial
<220> FEATURE:
<223> OTHER INFORMATION: primer

<400> SEQUENCE: 32
aaaaattcat atgataaaca gcccagatga cgcagcacac g                           41

<210> SEQ ID NO 33
<211> LENGTH: 27
<212> TYPE: DNA
<213> ORGANISM: artificial
<220> FEATURE:
<223> OTHER INFORMATION: primer

<400> SEQUENCE: 33
aaagctagca atagcagcct gccgcag                                           27

<210> SEQ ID NO 34
<211> LENGTH: 45
<212> TYPE: DNA
<213> ORGANISM: artificial
<220> FEATURE:
<223> OTHER INFORMATION: primer
```

```
<400> SEQUENCE: 34
aaaaattcat atgataaaca gcccagatga cgcagcacac gatag        45

<210> SEQ ID NO 35
<211> LENGTH: 36
<212> TYPE: DNA
<213> ORGANISM: artificial
<220> FEATURE:
<223> OTHER INFORMATION: primer

<400> SEQUENCE: 35
aaaaaagcta gcaatagcca gagctttctg ctgaaa        36

<210> SEQ ID NO 36
<211> LENGTH: 38
<212> TYPE: DNA
<213> ORGANISM: artificial
<220> FEATURE:
<223> OTHER INFORMATION: primer

<400> SEQUENCE: 36
aaaaattcat atgataaaca gcccagatga cgcagcac        38
```

CYCLIZED CYTOKINES AND METHOD FOR PRODUCING SAME

RELATED APPLICATIONS

This application is a divisional of U.S. patent application Ser. No. 15/566,365, filed Oct. 13, 2017, which is a 35 U.S.C. § 371 national phase entry of PCT Application PCT/JP2016/061923, filed Apr. 13, 2016, and published in Japanese on Oct. 20, 2016, as International Publication No. WO 2016/167291, and which claims the benefit of Japanese Application No. 2015-082018, filed Apr. 13, 2015, the disclosure of each of which is incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 5576-340_ST25.txt, 41,290 bytes in size, generated on Oct. 13, 2017, and filed via EFS-Web, is provided in lieu of a paper copy. This Sequence Listing is hereby incorporated by reference into the specification for its disclosures.

TECHNICAL FIELD

The present invention relates to novel improved versions of a pharmaceutically bioactive protein, preferably a cytokine with a helix bundle conformation, and more preferably granulocyte colony-stimulating factor (G-CSF), which acts to promote production of granulocytes and to enhance functions of neutrophils, nucleic acids encoding the improved proteins, and a production method therefor.

BACKGROUND ART (Protein Instability Problem when Used as Pharmaceutical)

When administered for treatment of humans, a bioactive protein often has an undesirable metabolic half-life. This intrinsic metabolic half-life frequently causes suboptimal therapeutic efficacy, medication compliance problems, and dosing schedule and administration regimen that are inconvenient for patients.
(Conventional Major Stability-Improving Strategies and their Problems)

In the production of a bioactive protein for treatment of humans, its metabolic half-life has been extended by physical means (e.g., alteration of an administration route, nanoparticle encapsulation, and liposome encapsulation), chemical modifications (e.g., emulsion, PEGylation, glycosylation), and modifications by genetic engineering (e.g., amino acid substitution, fusion to human serum albumin, incorporation of post-translational glycosylation) (Non-Patent Literatures 1 and 2). Unfortunately, most such approaches are expensive and entail additional time-consuming processes during production. In addition, PEG itself is immunogenic, so that anti-PEG antibodies are produced, resulting in a decrease in drug efficiency of a PEGylated protein and a decrease in safety, as disclosed in Non-Patent Literature 3.
(Cyclization-Medicated, Stability-Improving Approaches and their Problems)

Bioactive peptides each have a markedly shorter metabolic half-life than regular proteins. The metabolic half-life has been extended by cyclization of a certain linear peptide (Patent Literatures 1 and 2). In various conventional methods for producing a cyclized peptide, naturally occurring cyclized peptides have been mimicked and a biological process and a chemical process have been used in combination. For instance, cysteine residues have been introduced by chemical modification or genetic engineering modification so as to give a disulfide bond (Patent Literature 1). In another technology, a linear precursor molecule is produced in a cell (e.g., a bacterium); and an exogenous factor (e.g., an enzyme) is then added to make the linear precursor molecule cyclic by using a chemical process. In still another technology, a cyclized peptide is produced in a cell (e.g., a bacterium) by genetic engineering modification. For example, as described in Patent Literature 3, the transsplicing function of split inteins is exploited to make a precursor peptide cyclic, which is interposed between 2 parts of the split inteins.

In still another method, a cyclized peptide is produced through chemical modification by introducing unnatural amino acids and cross-linkers. For instance, a technology has been known which uses an olefin metathesis reaction to cross-link (S')-α-(2'-pentenyl) alanine residues, thereby making a peptide cyclized within a molecule (Patent Literature 4).

The above-mentioned cyclization methods are also used as a method for extending the metabolic half-life of not only peptides but also proteins. For proteins, which are more vulnerable to some chemical synthesis process than peptides, commonly used are modifications by genetic engineering or a protocol in which modifications by genetic engineering and chemical modifications under mild conditions are combined. However, such approaches each require addition of cross-linkers and amino acid sequence necessary for promoting a cyclization reaction to a wild-type protein. Generally speaking, when amino acids are substituted and/or inserted in a wild-type protein, the physical and biological characteristics of the protein are disturbed. Thus, it is important to complete a cyclization reaction without modifying the wild-type amino acid sequence whenever possible.

In addition, when reaction efficiency of the cyclization reaction is insufficient, an additional purification step of separating the resulting cyclized protein from an unreacted linear protein is needed. Between the cyclized protein and the unreacted linear protein, there are very little differences in their molecular weights and surface charges, so that it is uneasy to separate and purify them from each other. Meanwhile, the efficiency of the cyclization reaction depends on the characteristics of an exogenous factor (e.g., an enzyme) used for the cyclization reaction and the characteristics of a target protein that is subject to cyclization. There is no established common procedure to increase the efficiency.
(About Cytokine with Helix Bundle Conformation)

Among bioactive proteins for treatment of humans, cytokines such as granulocyte colony-stimulating factor (G-CSF) and erythropoietin have long been clinically applicable. These cytokines have a helix bundle conformation and increased three-dimensional homology. When stabilization of the conformation is used as a basis to extend its metabolic half-life, analogous approaches are often effective with respect to proteins with a similar conformation (Non-Patent Literature 4). In addition, the cytokines share structural features where their N-terminus and C-terminus are positioned closely, etc.
(About G-CSF)

Granulocyte colony-stimulating factor (G-CSF) is the hematopoietic factor that was discovered as a factor for inducing and differentiating a granulocyte stem cell and promotes production of neutrophils in vivo. Thus, G-CSF is clinically applicable as a drug for neutropenia after bone marrow transplantation and/or cancer chemotherapy. Various sources may be used to obtain and purify G-CSF. Glycosylated G-CSF, a product expressed in eukaryotic host cells, and non-glycosylated G-CSF, a product expressed in prokaryotic host cells, can be produced on an industrial scale. For instance, the former is lenograstim that is produced as a polypeptide chain with the same 174 amino acids as of a native protein. Then, the latter is filgrastim that is produced as a polypeptide chain with the same 175 amino acids as of the native protein except that a methionyl residue is added to the N-terminus. They are available for treatment use in several countries (Patent Literatures 5 and 6). Filgrastim has demonstrated that addition of a methionyl group to the N-terminus and a lack of glycosylation does not affect the functions of G-CSF. This is a known phenomenon. In addition, some reports said that a mutant in which amino acids positioned at the N-terminal region (1 to 17 residues) are replaced or deleted, and a mutant in which a peptide sequence having 12 amino acids is added to the C-terminus, retained the functions of G-CSF (Non-Patent Literatures 5 and 6). These reports indicate that the N-terminus and the C-terminus of G-CSF are tolerant to the introduction of mutations.

(Examples of Improving Stability of G-CSF)

Various modifications have been reported so as to extend the metabolic half-life of G-CSF. These modifications have been conducted by a technique in which amino acids are genetically replaced and modified or a technique in which PEGs, for example, are chemically added (Patent Literatures 7 and 8). For instance, the former is used for nartograstim that is produced as a polypeptide chain with the same 175 amino acids as of the native protein except that a methionyl residue is added to the N-terminus; the residues Thr2, Leu4, Gly5, Pro6, and Cys18 are replaced by Ala, Thr, Tyr, Arg, and Ser residues, respectively. The latter is used for pegfilgrastim that is a conjugated product of filgrastim and monomethoxy polyethylene glycol. They are available for treatment use in several countries. The PEGylation of filgrastim, like common PEGylation, has been demonstrated to result in an increase in stability but a decrease in activity thereof. For example, it has been shown that when compared with that of filgrastim, its metabolic half-life is increased from 1.79 h to 7.05 h (Patent Literature 7). By contrast, its activity is shown to be decreased to about 68 to 21% of that of filgrastim (Patent Literature 8).

In addition to the above, it has been reported (in Patent Literature 9) that by using the fact that the N-terminus and the C-terminus of G-CSF are closely positioned in its conformation, G-CSF has been modified to obtain a cyclized polypeptide chain such that a G-CSF, in which a plurality of Gly residues are added to the N-terminus and Leu, Pro, Xaa (Xaa is any amino acid), Thr, and Gly are added to the C-terminus, is expressed and isolated; and sortase A derived from *Staphylococcus aureus* is added thereto to chemically produce the cyclized polypeptide chain in vitro.

CITATION LIST

Patent Literature

Patent Literature 1: U.S. Pat. No. 4,033,940
Patent Literature 2: U.S. Pat. No. 4,102,877
Patent Literature 3: U.S. Pat. No. 7,846,710
Patent Literature 4: National Publication of International Patent Application No. 2008-501623
Patent Literature 5: U.S. Pat. No. 4,810,643
Patent Literature 6: U.S. Pat. No. 5,104,651
Patent Literature 7: U.S. Pat. No. 5,824,778
Patent Literature 8: U.S. Pat. No. 5,985,265
Patent Literature 9 U.S. Pat. No. 8,940,501

Non Patent Literature

Non Patent Literature 1: B. I. Lord, L. B. Woolford, and G. Molineux, Clin. Cancer Res., 2001, 7, 2085-90.
Non Patent Literature 2: P. van Der Auwera, E. Platzer, Z. X. Xu, R. Schulz, O. Feugeas, R. Capdeville, and D. J. Edwards, Am. J. Hematol., 2001, 66, 245-51.
Non Patent Literature 3: Guidance for Industry "Immunogenicity Assessment for Therapeutic Protein2", U. S. Department of Health and Human Services, Food and Drug Administration, August 2014, 1-36
Non Patent Literature 4: M. W. Popp, S. K. Dougan, T. Y. Chuang, E. Spooner, and H. L. Ploegh, Proc. Natl. Acad. Sci. U.S.A, 2011, 108, 3169-74.
Non Patent Literature 5: T. Kuga, Y. Komatsu, M. Yamasaki, S. Sekine, H. Miyaji, T. Nishi, M. Sato, Y. Yokoo, M. Asano, M. Okabe, M. Morimoto, and S. Itoh, Biochem. Biophys. Res. Commun., 1989, 159, 103-111.
Non Patent Literature 6: Y. Oshima, A. Tojo, Y. Niho, and S. Asano, Biochem. Biophys. Res. Commun., 2000, 267, 924-7.

SUMMARY OF INVENTION

Problems to be Solved by the Invention

The purpose of the present invention is to solve conventional technical problems in the production of a cyclized protein.

As described above, in the production of a cyclized peptide or a cyclized protein, the same procedure is used in each case in which a linear polypeptide is once synthesized and a chemical or biological process is then used to carry out a cyclization reaction. At this time, addition of a sequence for the cyclization reaction to a wild-type amino acid sequence may cause an unexpected change in the physical and biological characteristics of a target protein. In addition, if a linear polypeptide is contaminated as a by-product due to low cyclization reaction efficiency, a subsequent purification step is generally difficult. As a result, a target substance with high purity cannot be obtained.

The present invention addresses the problem of establishing a production method such that in the production of a cyclized protein, high cyclization reaction efficiency can be achieved and the number of amino acids added is minimal, thereby capable of retaining the biological characteristics of an original protein and providing a high-purity cyclized protein.

In particular, the present invention addresses the problem of establishing a method for producing a high-purity cyclized molecule modified by adding the minimum number of amino acids to a cytokine (e.g., G-CSF), a very stable modified version of which should be developed as a pharmaceutical, and providing the high-purity cyclized cytokine.

Means for Solving the Problems

The present inventors considered, as a cyclization efficiency-determining factor, how closely the N-terminus and the C-terminal are positioned in the conformation of a protein that is subject to cyclization. From this viewpoint, cyclized proteins having various modifications at their terminal sequences were designed and synthesized.

Specifically, a group of novel cyclized cytokines designed from the above viewpoint were produced and the cyclization efficiencies thereof were compared. In addition, the structure and function of each cyclized cytokine purified were examined in detail and were compared with those of a linear cytokine counterpart. This comparison showed that each cyclized cytokine had comparable functions and was very stable.

That is, the present application provides the following aspects of the present invention.

<1> A method for producing a cyclized mutant protein with biological properties not less than those of an original protein and with stability higher than that of the original protein by modifying, through the following steps (i) to (v), the original protein with a specific three-dimensional structure, the method comprising the steps of:

(i) determining, based on conformational information about the original protein, secondary structure-free regions at an N-terminal portion or a C-terminal portion of the original protein and determining an N-terminus and a C-terminus of a secondary structure-forming portion of the original protein if the secondary structure-free regions are deleted;

(ii) screening a protein database for proteins with secondary structures similar to those of N-terminal residues and C-terminal residues of the secondary structure-forming portion;

(iii) determining, based on results of the screening, an amino acid length of a loop structure through which the N-terminus and the C-terminus of the secondary structure-forming portion of the original protein are to be connected;

(iv) designing and producing a linear mutant protein that can be subjected to cyclization so as to obtain a cyclized mutant protein in which the N-terminus and the C-terminus of the secondary structure-forming portion of the original protein are connected via the loop structure with the amino acid length determined; and (v) linking an N-terminus and a C-terminus of the linear mutant protein by a chemical or biological method so that the cyclization is made to obtain the cyclized mutant protein.

<2> The method for producing a cyclized mutant protein according to item<1>, wherein the cyclization of step (v) uses a trans-splicing reaction mediated by split inteins.

<3> The method for producing a cyclized mutant protein according to item<1> or <2>, wherein the original protein with a specific three-dimensional structure is a cytokine with a helix bundle structure and the biological properties of the original protein involve affinity for a receptor.

<4> The method of producing a cyclized mutant protein according to item<3>, wherein the original protein with a specific three-dimensional structure is granulocyte colony-stimulating factor (G-CSF).

<5> A cyclized mutant protein produced using the production method according to any one of items (1) to (4).

<6> A cyclized mutant protein consisting of an amino acid sequence in which secondary structure-free regions at an N-terminal portion or a C-terminal portion of an original protein with a specific three-dimensional structure are deleted and a predetermined number of amino acid residues is added to each of an N-terminus and a C-terminus of a secondary structure-forming portion of the original protein after the deletion, wherein the predetermined number of amino acid residues is the number of amino acid residues, the number corresponding to the number of amino acids connecting secondary structures of N-terminal residues and C-terminal residues of a secondary structure-forming portion of another protein, the secondary structures being similar to those of the secondary structure-forming portion of the original protein.

<7> The cyclized mutant protein according to item<6>, wherein the protein with a specific three-dimensional structure is a cytokine with a helix bundle structure.

<8> The cyclized mutant protein according to item<6> or <7>, wherein the original protein with a specific three-dimensional structure is a granulocyte colony-stimulating factor (G-CSF) consisting of an amino acid sequence set forth in SEQ ID NO: 1; 0 to 11 amino acid residues are deleted from an N-terminus of the amino acid sequence set forth in SEQ ID NO: 1; 0 to 3 amino acid residues are deleted from an C-terminus of the amino acid sequence; a serine or cysteine residue is added to an N-terminus and/or a C-terminus of the amino acid sequence after the deletion; and an amino acid residue other than proline is added to the C-terminus of the amino acid sequence after the deletion.

<9> The cyclized mutant protein according to any one of items<6> to <8>, wherein the protein consists of a cyclized amino acid sequence set forth in any one of SEQ ID NOs: 6 to 9.

<10> A linear mutant protein designed so as to produce the cyclized mutant protein according to any one of items<6> to <9>, wherein the linear mutant protein consists of an amino acid sequence in which secondary structure-free regions at an N-terminal portion and a C-terminal portion of an original protein with a specific three-dimensional structure are deleted and a predetermined number of amino acid residues is added to each of an N-terminus and a C-terminus of a secondary structure-forming portion of the original protein after the deletion; the predetermined number of amino acid residues is the number of amino acid residues, the number corresponding to the number of amino acids connecting secondary structures of N-terminal residues and C-terminal residues of a secondary structure-forming portion of another protein, the secondary structures being similar to those of the secondary structure-forming portion of the original protein; and a most N-terminus amino acid residue and a most C-terminus amino acid residue of the predetermined number of amino acid residues added are amino acid residues that enable the linear mutant protein to be subject to cyclization.

<11> The linear mutant protein according to item<10>, wherein the protein is designed so as to produce the cyclized mutant protein according to item<9> and consists of an amino acid sequence set forth in any one of SEQ ID NOs: 2 to 5.

<12> The linear mutant protein according to item<10>, wherein the protein is designed so as to produce the cyclized mutant protein according to item<9> by using, as split inteins, DnaE-C(C-intein) and DnaE-N(N-intein) of DnaE derived from *Nostoc punctiforme* and consists of an amino acid sequence set forth in any one of SEQ ID NOs: 10 to 13.

<13> A nucleic acid comprising a nucleotide sequence encoding an amino acid sequence of the mutant protein according to any one of items<5> to <12>.

<14> A recombinant vector comprising the nucleic acid according to item<13>.

<15> A transformant comprising the recombinant vector according to item<14>.

<16> A method for producing the mutant protein according to any one of items<5> to <12>, using the transformant according to item<15>.

<17> A pharmaceutical composition comprising, as an active ingredient, the mutant protein according to any one of items<5> to <12>.

<18> A pharmaceutical composition for treatment of neutropenia, comprising, as an active ingredient, the mutant protein according to any one of items<5> to <12>.

Advantageous Effects of Invention

In the present invention, specifically developed is G-CSF (C177), a cyclized protein composed of an amino acid sequence in which only 2 amino acids are added to a linear control G-CSF. In addition, G-CSF(C163) is a cyclized protein composed of an amino acid sequence in which nonstructural regions at the N-terminus and the C-terminus are deleted and only 2 amino acids are added. Further, G-CSF(C166) or G-CSF(C170) is a cyclized protein composed of an amino acid sequence in which nonstructural regions at the N-terminus and the C-terminus are deleted and 5 or 9 amino acid residues, respectively, are added.

When compared with commercially available filgrastim and the linear control G-CSF, any of them can maintain intrinsic receptor-binding activity and have increased thermostability and protease resistance. Among them, G-CSF (C163), G-CSF(C166), and G-CSF(C170) were able to achieve high cyclization efficiency while the number of amino acids added is small.

Currently, G-CSF has been widely used in clinical practice including treatment of neutropenia caused by cancer chemotherapy. Development of biobetter drugs is in progress so as to enhance stability by using a variety of strategies such as a mutant G-CSF and a chemically-modified G-CSF. Among the strategies, a polypeptide chain cyclization technique aims at increasing stability while change in the amino acid sequence and change in the conformation of a protein can be minimized. An undesirable characteristic change such as an increase in immunogenicity can also be minimized. Thus, the technique seems to have a substantial advantage in the production of bioactive proteins for treatment of humans.

According to the present invention, it is possible to reduce, to minimum, addition of a sequence necessary for a cyclization reaction, which addition is the biggest disadvantage in increasing stability by cyclization in view of the above-described situations. Further, the present invention can resolve the problems of low cyclization reaction efficiency and a complicated purification step, thereby significantly contributing to technical advances in the art.

BRIEF DESCRIPTION OF DRAWINGS

FIG. 1. The amino acid sequence of filgrastim (SEQ ID NO: 14) and the amino acid sequence of a linear control G-CSF (SEQ ID NO: 1), some amino acids of which are replaced in the sequence of filgrastim, are compared to the amino acid sequences of four different cyclized G-CSFs designed (C177 (SEQ ID NO:2); C170 (SEQ ID NO:3); C166 (SEQ ID NO:4); C163 (SEQ ID NO: 5)). The schematic diagram shown at the top row shows helix-forming regions predicted on the basis of a known G-CSF conformation (PDB code: 2D9Q).

FIG. 2 is a synthetic scheme for a cyclized G-CSF produced using inteins.

FIG. 3 is an SDS-PAGE picture showing a group of modified cyclized G-CSFs (G-CSF(C177) and G-CSF(C163)) after purification.

FIG. 4 is sensorgrams obtained by measuring, by means of surface plasmon resonance, the binding activity of each modified cyclized G-CSF (G-CSF(C177) or G-CSF(C163)) toward a G-CSF receptor.

FIG. 5 is graphs showing the activity of each modified cyclized G-CSF (G-CSF(C177) or G-CSF(C163)) on cells.

FIG. 6 is a graph obtained by measuring, by means of circular dichroism, the thermostability of each modified cyclized G-CSF (G-CSF(C177) or G-CSF(C163)).

FIG. 7 is a graph in which the protease resistance of each modified cyclized G-CSF (G-CSF(C177) or G-CSF(C163)) was evaluated using the remaining amount thereof after a reaction.

FIG. 8 is electron density maps of terminal regions of each modified cyclized G-CSF (G-CSF(C177) or G-CSF (C163)), which regions were subjected to cyclization and are visualized by X-ray crystallography.

FIG. 9 is SDS-PAGE pictures showing, among the modified cyclized G-CSFs, G-CSF(C170) and G-CSF(C166) after purification by size-exclusion chromatography.

FIG. 10 is sensorgrams obtained by measuring, by means of surface plasmon resonance, the binding activity of each of G-CSF(C170), G-CSF(C166), and filgrastim among the modified cyclized G-CSFs toward a G-CSF receptor, and sensorgrams obtained by re-measuring the binding activity of each of the linear control G-CSF, G-CSF(C177), and G-CSF(C163) toward the G-CSF receptor.

FIG. 11 is a graph obtained by measuring, by means of circular dichroism, the thermostability of each of G-CSF (C170) and G-CSF(C166) among the modified cyclized G-CSFs, and a graph obtained by re-measuring the thermostability of each of the linear control G-CSF, G-CSF(C177), and G-CSF(C163).

FIG. 12 is a graph in which the protease resistance of each of G-CSF(C170) and G-CSF(C166) among the modified cyclized G-CSFs was evaluated using the remaining amount thereof after a reaction.

MODE FOR CARRYING OUT THE INVENTION (Cyclized Mutant Protein and Production Method Thereof)
In a production method according to an aspect of the present invention, an original protein with a specific three-dimensional structure is modified to obtain a cyclized mutant protein after the following steps (i) to (v):

(i) determining, based on conformational information about the original protein, secondary structure-free regions at an N-terminal portion or a C-terminal portion of the original protein and determining an N-terminus and a C-terminus of a secondary structure-forming portion of the original protein if the secondary structure-free regions are deleted;

(ii) screening a protein database for proteins with secondary structures similar to those of N-terminal residues and C-terminal residues of the secondary structure-forming portion;

(iii) determining, based on results of the screening, an amino acid length of a loop structure through which the N-terminus and the C-terminus of the secondary structure-forming portion of the original protein are to be connected;

(iv) designing and producing a linear mutant protein that can be subjected to cyclization so as to obtain a cyclized mutant protein in which the N-terminus and the C-terminus of the secondary structure-forming portion of the original protein are connected via the loop structure with the amino acid length determined; and (v) linking an N-terminus and a C-terminus of the linear mutant protein by a chemical or biological method so that the cyclization is made to obtain the cyclized mutant protein.

Hereinbelow, disclosed is a method for producing a cyclized mutant protein when granulocyte colony-stimulating factor (G-CSF) is used as an original protein with a specific three-dimensional structure. The present production method is not limited to this embodiment, and is widely applicable to cyclization of various proteins. The present production method is applicable to cyclization of any protein as long as the amino acid sequence of the protein is known and its conformation (three-dimensional structure) is already determined. In particular, from the viewpoint of cyclization efficiency, preferred is cyclization of a protein, the N-terminus and the C-terminus of which are positioned closely in its conformation. Here, G-CSF is known to have a helix bundle structure as its three-dimensional structure. The present production method seems to particularly fit cyclization of a protein (e.g., erythropoietin, interferon α) with the same helix bundle structure as of G-CSF. Those skilled in the art can carry out cyclization of another protein by using substantially the same technique as the present production method when the below-described G-CSF cyclization technique is taken into consideration. This production method enables very efficient cyclization while the number of amino acids added is minimal. Also, the secondary structure of a cyclized mutant protein as obtained using this production method does not change from that of an original protein. This yields such advantages as the biological properties of the original protein being retained and the stability being higher than that of the original protein.

(Description of G-CSF)

Granulocyte colony-stimulating factor (G-CSF) is a cytokine that binds to a granulocyte colony-stimulating factor receptor (G-CSF receptor) to induce production of neutrophils, etc., and is used for treatment of neutropenia during cancer chemotherapy, etc. While G-CSF is very useful in treatment, it unfortunately has low stability. Accordingly, efforts have been made to increase its stability (Reference Document 1). It is known that the N-terminus and the C-terminus of G-CSF is positioned closely in its three-dimensional structure. It has been reported that when the termini are linked by a covalent bond, the thermostability increases (Reference Document 2).

In the present invention, a linear polypeptide consisting of 175 amino acids set forth in SEQ ID NO: 1 was used as a linear control G-CSF, a starting material for improvement. When the amino acid sequence of the linear control G-CSF is compared with the amino acid sequence (SEQ ID NO: 14) of filgrastim, threonine at position 2 and cysteine at position 18 are replaced by alanine and serine, respectively. A previous report has demonstrated that these mutations do not affect the activity of G-CSF (Reference Document 3).

(Description of Mutants Developed Herein)

Improved proteins developed herein each consist of an amino acid sequence that is human-designed on the basis of the amino acid sequence of the linear control G-CSF, and can be produced highly efficiently as a cyclized molecule without impairing the G-CSF receptor-binding activity while the number of amino acids added is minimal.

(Sequences of Specific Mutants Developed Herein)

Four different improved proteins developed and designed herein are composed of the respective four different amino acid sequences described below (FIG. 1).

G-CSF(C177) is a polypeptide consisting of 177 amino acids set forth in SEQ ID NO: 2, and an amino group of serine at the N-terminus and a carbonyl group of glycine at the C-terminus are linked by a peptide bond as shown in SEQ ID NO: 6. The amino acid sequence set forth in SEQ ID NO: 2 corresponds to a sequence in which serine is added at the N-terminus and glycine is added to the C-terminus of the amino acid sequence (SEQ ID NO: 1) of the linear control G-CSF.

G-CSF(C170) is a polypeptide consisting of 170 amino acids set forth in SEQ ID NO: 3, and an amino group of serine at the N-terminus and a carbonyl group of glycine at the C-terminus are linked by a polypeptide bond as shown in SEQ ID NO: 7. The amino acid sequence set forth in SEQ ID NO: 3 corresponds to a sequence in which N-terminal 4 amino acid residues and C-terminal 3 amino acid residues are deleted from the amino acid sequence (SEQ ID NO: 1) of the linear control G-CSF and serine is added to its N-terminus and glycine is added to its C-terminus.

G-CSF(C166) is a polypeptide consisting of 166 amino acids set forth in SEQ ID NO: 4, and an amino group of serine at the N-terminus and a carbonyl group of glycine at the C-terminus are linked by a peptide bond as shown in SEQ ID NO: 8. The amino acid sequence set forth in SEQ ID NO: 4 corresponds to a sequence in which N-terminal 8 amino acid residues and C-terminal 3 amino acid residues are deleted from the amino acid sequence (SEQ ID NO: 1) of the linear control G-CSF and serine is added to its N-terminus and glycine is added to its C-terminus.

In addition, G-CSF(C163) is a polypeptide consisting of 163 amino acids set forth in SEQ ID NO: 5, and an amino group of serine at the N-terminus and a carbonyl group of glycine at the C-terminus are linked by a polypeptide bond as shown in SEQ ID NO: 9. The amino acid sequence set forth in SEQ ID NO: 5 corresponds to a sequence in which N-terminal 11 amino acid residues and C-terminal 3 amino acid residues are deleted from the amino acid sequence (SEQ ID NO: 1) of the linear control G-CSF and serine is added to its N-terminus and glycine is added to its C-terminus.

(Concerning Addition of Amino Acids to N-Terminus and C-Terminus so as to Carry Out Cyclization Reaction)

To make a protein cyclic in accordance with the present invention, it is possible to use an intracellular cyclization reaction using inteins. DnaE derived from *Nostoc punctiforme* can be used as the inteins. More specifically, it is possible to use DnaE-C and DnaE-N, proteins consisting of amino acid sequences set forth in SEQ ID NOs: 15 and 16, respectively. A polypeptide chain in which a target protein is interposed between the DnaE-C and the DnaE-N is subject to spontaneous splicing using DnaE autocatalytic function, thereby synthesizing a cyclized protein in which an amino group at the N-terminus and a carbonyl group at the C-terminus of the target protein are linked by a peptide bond (by means of split inteins; see FIG. 2).

Use of split inteins requires cysteine or serine at either the N-terminus or the C-terminus of a target protein as well as proline at the C-terminus markedly decreases reaction efficiency (Reference Document 6). Because of this, in the cases of the above-mentioned present improved proteins, serine is added to the N-terminus and glycine is added to the C-terminus of the target protein. However, amino acids usable at the N-terminus or the C-terminus are not limited to the above amino acids. In addition to the above combination, 78 different sequence combinations may each be a choice. Whether the sequence combination is good or poor may be evaluated by a method for comparing proteins actually synthesized and purified. In addition, it is possible to use a method including: replacing, on a model, a loop region of a known conformation described below by each corresponding sequence; and computationally comparing the free energies thereof.

In the cases of the improved G-CSFs, the present inventors designed, from the above viewpoint, a sequence (SEQ ID NO: 2) in which serine is added to the N-terminus and glycine is added to the C-terminus of the amino acid sequence (SEQ ID NO: 1) of the linear control G-CSF, and produced G-CSF(C177) by using split inteins. G-CSF (C177) had G-CSF receptor-binding activity comparable to that of the linear control G-CSF and exhibited better activity in cells, thermostability, protease resistance, and metabolic half-life, but exhibited somewhat low cyclization efficiency (see Table 1).

(To Select Sequences Deleted from N-terminus and C-terminus of Original Protein (Step (i)))

In order to modify an original protein to obtain substantially the same biological activity as that of the original protein, it is important not to damage the conformation of the original protein. Also, to achieve high cyclization efficiency, it seems to be critical that the N-terminus and the C-terminus of the modified protein is positioned closely in its conformation.

To design an improved G-CSF from such viewpoint, the present inventors did remove conformationally disordered regions from the N-terminal sequence and the C-terminal sequence of the original protein. Specifically, in the known G-CSF conformation model, a secondary structure-forming region is determined to be a conformationally stable region and a secondary structure-free region is determined to be a disordered region. More specifically, 11 amino acids from methionine at position 1 to proline at position 11 and 3 amino acids from alanine at position 173 to proline at position 175 of the amino acid sequence (SEQ ID NO: 1) of the linear control G-CSF were determined to be secondary structure-free regions and were then removed.

Reference Documents 4 and 5 report a plurality of algorithms used to determine a secondary structure-forming region in conformation modeling. Their determination often gives different results with respect to a terminal portion of the secondary structure. Accordingly, different algorithms adopted result in different candidates for a cleavage site. In addition, to determine the disordered region, it is possible to use a molecular dynamics technique to calculate a change in the structure of the terminal portion. When different methods give different determination results, it is reasonable to adopt a representative value obtained by statistical processing. As the representative value, preferred is a mode. If there are different results, a value at which the secondary structure-forming region is minimal is adopted.

If information on the conformation of some protein other than G-CSF is available, secondary structure-free regions at the N-terminus and the C-terminus are likewise determined. Then, the N-terminus and the C-terminus of the protein when the secondary structure-free regions are deleted (i.e., the N-terminus and the C-terminus of the secondary structure-forming portion) can be determined. Note that in this step, it is not necessary to actually remove a secondary structure-free region from a protein by means of deletion and mutation, etc. It is simply sufficient to determine, in a design simulation, the N-terminus and the C-terminus thereof while considering only a secondary structure-forming region without considering secondary structure-free regions.

(Loop Design)

Of the two termini of a protein after secondary structure-free regions at the two termini have been removed, each has a secondary structure, so that it seems to be difficult to link the termini as they are and to make the protein cyclic. Then, the present inventors added, to each terminus, amino acid residues (or a sequence) used to form a loop with an appropriate length so as to connect these termini after conformationally disordered regions have been removed from the N-terminal sequence and the C-terminal sequence of G-CSF for cyclization. Note that as used herein, the loop refers to a portion composed of an amino acid sequence connecting both the termini of the protein after the secondary structure-free regions have been removed from the original termini (i.e., connecting the N-terminus and the C-terminus of a secondary structure-forming portion of a protein of interest).

The appropriate length of the loop was determined using the following procedure.

(Screening for Analogous Proteins (Step (ii)))

First, from protein conformations registered in a database, a group of proteins with a "helix-loop-helix" secondary structure in which two helices are connected via a loop was retrieved and a group of proteins with structural homology to G-CSF was further selected. Specifically retrieved was a group of proteins with a helix-loop-helix structure in which proximal 4-amino-acid portions (total of 8 amino acids) adjacent to the loop between the two helices are structurally similar to 4-amino-acid portions (total of 8 amino acids) at the corresponding G-CSF helix termini (i e, the N-terminus and the C-terminus of the secondary structure-forming region after the secondary structure-free regions have been removed). For example, when 4 amino acid residues (α-carbon atom) positioned at each of the two helix terminal portions of G-CSF and those of a subject protein are superimposed, their root mean square deviation may be less than 1.5 Å and preferably less than 1 Å. In this case, the subject protein can be retrieved as a structurally similar protein. In this regard, however, the amino acid residue lengths at both the helix termini being compared herein do not have to be 4, and may be adjusted to, for example, a range from 1 to 10 and preferably from 3 to 6 depending on how many proteins have a helix-loop-helix structure being selected based on structural similarity. That is, if the amino acid residue lengths at both the helix termini being compared are short, the number of the structurally similar proteins being selected becomes large, and if the amino acid residue lengths are long, the number of the structurally similar proteins being selected becomes small. Because of this, the amino acid lengths at both the helix termini being compared may be suitably adjusted such that the number of the structurally similar proteins being selected is set to a desirable degree (e.g., within 100 to within 1000 and preferably from about 50 to 100). For example, Protein Data Bank (PDB; rcsb.org/) is available as the database. Examples of a condition that is for a group of proteins retrieved from the database and can be added include the degree of resolution of protein conformation (e.g., 3.0 Å or more and preferably 2.5 Å or more).

Like in the case of G-CSF, the database may be screened for proteins with secondary structures similar to those of N-terminal residues and C-terminal residues of a secondary structure-forming region of any protein other than G-CSF.

(To determine the Length of Loop (Step (iii)))

Next, how many amino acid residues a loop of each protein selected as having high structural homology to G-CSF had was analyzed. As a result, it was observed that the number of amino acid residues of the loop was mostly 2, 5, or 9 (22% of all the loops had 2 amino acid residues; 26% of all had 5 amino acid residues; and 16% of all had 9 amino acid residues). In view of the above, it was predicted that a modified cyclized molecule with the smallest size could be constructed using a procedure in which the nonstructural regions at the N-terminus and the C-terminus of G-CSF had been removed and two amino acids were added to the resulting G-CSF. Further, it was also predicted that a stable modified cyclized molecule could be constructed by adding five or nine amino acids.

The amino acid length of a loop structure through which the N-terminus and the C-terminus of a secondary structure-forming portion of a protein other than G-CSF can be determined such that the amino acid length corresponds to the number of amino acids used to connect corresponding secondary structure portions of another protein having similar secondary structure portions as obtained as a result of the screening. Specifically, the screening results in the number of amino acids used to connect, to each other, secondary structure portions of each of analogous proteins having high structural homology. Among the numbers, the frequently occurring amino acid length is determined to be the amino acid length (loop length) of a loop structure through which the N-terminus and the C-terminus of a secondary structure-forming portion of a protein subjected to cyclization is to be connected. How frequently the amino acid length to be selected as the loop length occurs may be selected by adopting the number of amino acids used to connect, to each other, the secondary structure portions, the number occurring in 10% or more and preferably 15% or more of the proteins screened out. When there are several frequently occurring amino acid lengths, one of the amino acid lengths may be selected. To construct a modified cyclized molecule with a minimum size, the amino acid length of the loop structure is preferably as short as possible. However, a shorter one does not necessarily mean that it will be a better one. From the viewpoint of stability and cyclization efficiency, it is desirable to select a suitable length. This step makes it possible to determine an optimal loop length so as to connect the N-terminus and the C-terminus of a secondary structure-forming portion of a protein without changing its structure.

(To Design Linear Mutant Protein and Make It Cyclic (Steps (iv) and (v))

Based on the above prediction, N-terminal 11 amino acid residues and C-terminal 3 amino acid residues (i.e., secondary structure-free regions) were deleted from the amino acid sequence (SEQ ID NO: 1) of the linear control G-CSF. In addition, serine and glycine (total of 2 amino acid residues) were added to the N-terminus and the C-terminus, respectively, to design a sequence (SEQ ID NO: 5). Next, split inteins were used to produce G-CSF(C163) with a loop length of 2 amino acids. G-CSF(C163) had G-CSF receptor-binding activity comparable to that of the linear control G-CSF and exhibited somewhat poorer activity on cells, thermostability, protease resistance, and metabolic half-life than G-CSF(C177), but exhibited high cyclization efficiency (100%) (see Table 1).

From these results, it can be predicted that any modified cyclized molecule having a longer amino acid sequence than G-CSF(C163) and a shorter amino acid sequence than G-CSF(C177) has substantially the same preferable properties as of G-CSF(C177) and G-CSF(C163). In particular, modified cyclized molecules in which the loop length has been adjusted to 9 or 5 amino acids are highly likely to have improved cyclization reaction efficiency and enhanced stability while maintaining the structure of the linear control G-CSF.

When kinds of amino acids constituting the loop are determined, an available sequence is limited depending on a technique used for cyclization. For instance, when split inteins are used, it has already been shown that cysteine or serine at either the N-terminus or the C-terminus of a target protein is essential and proline at the C-terminus markedly decreases reaction efficiency (Reference Document 6). Hence, an amino acid residue added to form a loop after cyclization (or a terminal residue of an amino acid sequence) should be cysteine or serine at either the N-terminus or the C-terminus, and the C-terminal residue should not be proline.

(To Improve Loops)

Based on the above prediction, modified molecules were produced in which the loop length was adjusted to nine or five amino acids. Seven or three amino acids, except for serine and glycine at the N-terminus and the C-terminus, respectively, which are amino acid residues required for cyclization using split inteins, were designed so as to maintain the amino acid sequence of the linear control G-CSF as much as possible. Specifically, N-terminal 4 amino acid residues and C-terminal 3 amino acid residues of the amino acid sequence (SEQ ID NO: 1) of the linear control G-CSF were deleted; serine was added to the N-terminus and glycine was added to the C-terminus to give an engineered sequence (SEQ ID NO: 3); and split inteins were used to produce G-CSF(C170) with a loop length of 9 amino acids. Similarly, N-terminal 8 amino acid residues and C-terminal 3 amino acid residues of the amino acid sequence (SEQ ID NO: 1) of the linear control G-CSF were deleted; serine was added to the N-terminus and glycine was added to the C-terminus to give an engineered sequence (SEQ ID NO: 4); and split inteins were used to produce G-CSF(C166) with a loop length of 5 amino acids.

Both G-CSF(C170) and G-CSF(C166) had G-CSF receptor-binding activity comparable to that of the linear control G-CSF and had higher thermostability than G-CSF(C177). In addition, the cyclization efficiency was equal to or somewhat lower than that of G-CSF(C163), but was markedly higher than that of G-CSF(C177) (see Table 3). In particular, the thermostability of G-CSF(C166) was markedly higher than other modified molecules. Accordingly, its loop length is considered to be optimal for stabilization of the structure of G-CSF.

From these results, it can be predicted that any modified cyclized molecules having an amino acid sequence longer than G-CSF(C163) and shorter than G-CSF(C177) have likewise preferable properties, the molecules being modified G-CSF cyclized molecules each having an amino acid sequence in which 0 to 11, and preferably 1 to 11, amino acid residues are deleted from the N-terminus and 0 to 3, and preferably 1 to 3, amino acid residues were deleted from the C-terminus of the amino acid sequence set forth in SEQ ID NO: 1; a serine or cysteine residue is added to the N-terminus and/or the C-terminus after the deletion; an amino acid residue other than proline is added to the C-terminus.

For proteins other than G-CSF, a loop structure having a determined amino acid length is used to connect the N-terminus and the C-terminus of a secondary structure-forming portion of a protein of interest to obtain a cyclized mutant protein. For this purpose, a linear mutant protein that can be made cyclic may be designed and produced and then the N-terminus and the C-terminus of the linear mutant protein may be subjected to cyclization and be linked to obtain a cyclized mutant protein.

The linear mutant protein is designed such that a portion of the loop structure-forming amino acid sequence is added to the N-terminus and the rest is added to the C-terminus of the amino acid sequence of a secondary structure-forming portion of an original protein. The total of the number of amino acid residues added to the N-terminus and the number of amino acid residues added to the C-terminus should be the amino acid length of the loop structure determined above. Preferable design is such that at least one amino acid residue is added to each of the N-terminus and the C-terminus of a secondary structure-forming portion of an original protein.

Here, the loop structure-forming amino acid sequence is preferably designed such that the amino acid sequence of the secondary structure-free region removed, on the basis of the design concept, in step (i) is replaced by the necessary number of amino acids. That is, it is preferable that the amino acid sequence of the loop structure portion is designed so as to maintain the amino acid sequence of the original protein as much as possible. From the viewpoint of using, as a pharmaceutical composition, the resulting cyclized mutant protein, it is desirable to design so as to maintain the same conformation as that of the original protein as much as possible.

In this regard, however, at least the amino acid residues of the linear mutant protein nearest the N-terminal and nearest the C-terminal should be amino acid residues necessary for cyclization. As described above, when split inteins are used for cyclization, either the nearest N-terminal residue or the nearest C-terminal residue is cysteine or serine, and the nearest C-terminal residue is an amino acid residue other than proline.

Hence, in this case, the design may be such that the amino acid length of the remaining secondary structure-free region of the original protein plus the number of amino acid residues necessary for cyclization (when split inteins are used, the total number of amino acid residues nearest the N-terminal side and nearest the C-terminal side is two) equals the amino acid length of the loop structure determined above.

In other words, the linear mutant protein or cyclized mutant protein as obtained by the above production method can be said to have an amino acid sequence in which a predetermined number of amino acid residues is deleted from a portion of the secondary structure-free region at each of the N-terminus and the C-terminus of the original protein; after the deletion, amino acid residues necessary for cyclization are added to each of the N-terminus and the C-terminus. As a result, the conformation of the original protein can remain the same as much as possible and an increase in the cyclization efficiency can be achieved while the number of amino acids added is minimal.

(About Other Cyclization Techniques)

When cyclization techniques other than the technique using inteins are used, loop sequence design conditions are different. For instance, when a disulfide bond is used for cyclization, cysteine is added to each of the N-terminus and the C-terminus. In addition, when the sortase-mediated formation of an isopeptide bond is used for cyclization, it is essential to design a loop with an amino acid sequence suitable for the substrate specificity of a sortase used. Specifically, when *Staphylococcus aureus*-derived sortase A is used, a loop region should have a plurality of Gly residues at the N-terminus and a sequence containing Leu, Pro, Xaa (Xaa is any amino acid), Thr, and Gly at the C-terminus.

(To Produce Improved Protein)
(1) To Produce Improved Protein by Using Genetic Engineering Technique.
a. Gene Encoding Improved Protein In the present invention, a genetic engineering method can be used to produce the improved proteins designed above.

Specific examples of the gene used, in such a method, for each improved G-CSF include nucleic acids encoding the amino acid sequences set forth in SEQ ID NOs: 2, 3, 4, and 5 as described above. The nucleic acids are not limited to the above as long as the nucleic acids each encode a protein having substantially the same G-CSF receptor-binding activity as of each improved G-CSF.

Examples may include: nucleic acids encoding proteins each having G-CSF receptor-binding activity and having an amino acid sequence in which one or several amino acid residues are deleted from, replaced in, or added to the amino acid sequence set forth in SEQ ID NO: 2, 3, 4, or 5 except that the amino acid residues added to the N-terminus and the C-terminus so as to perform the above-described cyclization reaction remain intact; and nucleic acids encoding proteins each having said amino acid sequence in which the residue at either the N-terminus or C-terminus is changed to cysteine or serine and the residue at the C-terminus is changed to an amino acid other than proline.

Examples of such genes include nucleic acids, each consisting of the nucleotide sequence set forth in SEQ ID NO: 17, 18, 19, or 20.

Also, examples of the gene used in the present invention include a gene, the nucleic acid of which is hybridized, under stringent conditions, with a sequence complementary to the sequence of a nucleic acid encoding the amino acid sequence set forth in SEQ ID NO: 2, 3, 4, or 5 except for a portion encoding the amino acid residues added at the N-terminus and the C-terminus so as to perform the above-described cyclization reaction, and in which a nucleic acid encoding cysteine or serine is added to either the N-terminus or the C-terminus of a nucleic acid encoding a protein having G-CSF receptor-binding activity and a nucleic acid encoding an amino acid other than proline is added to the C-terminus. As used herein, the term "stringent conditions" refers to a condition under which a specific hybrid is formed and no non-specific hybrid is formed. For instance, the stringent conditions refers to condition under which a nucleic acid having high homology (the homology is 60% or higher and preferably 80% or higher) is hybridized therewith. More specifically, the concentration of sodium is from 150 to 900 mM and preferably from 600 to 900 mM and the temperature is from 60 to 68° C. and preferably 65° C. in that condition. For example, the hybridization is performed at 65° C. and the washing is performed in 0.1% SDS-containing 0.1×SSC at 65° C. for 10 min. In such conditions, when the hybridization is demonstrated by a conventional technique (e.g., Southern blotting, dot-blot hybridization), it can be said that the hybridization under the stringent condition occurs.

In addition to the above, a gene used for the cyclization reaction consists of a nucleic acid encoding a protein having an amino acid sequence (SEQ ID NO: 10, 11, 12, or 13) in which 2 amino acid sequences set forth in SEQ ID Nos: 15 and 16 are linked to the N-terminus and the C-terminus of the amino acid sequence set forth in SEQ ID NO: 2, 3, 4, or 5, or having an amino acid sequence in which the above-described modification is added to the amino acid sequence set forth in SEQ ID NO: 2, 3, 4, or 5 or an amino acid sequence encoded by a nucleic acid as obtained by adding the above-described modification to a nucleic acid hybridized, under stringent conditions, with a nucleic acid encoding the amino acid sequence set forth in SEQ ID NO: 2, 3, 4, or 5; and having an amino acid sequence in which 2 amino acid sequences set forth in SEQ ID NOs: 15 and 16 are linked to the N-terminus and the C-terminus of the amino acid sequence of a protein having G-CSF receptor-binding activity and having a function that makes the amino acid sequence sandwiched between SEQ ID NOs: 15 and 16 cyclic as a result of an autocatalytic process.

Examples of such genes include nucleic acids, each consisting of the nucleotide sequence set forth in SEQ ID NO: 21, 22, 23, or 24.

b. To Produce Genes, Recombinant Vectors, and Transformants

Genes according to the present invention can be synthesized using chemical synthesis, a PCR method, a cassette mutation method, site-specific mutagenesis, etc. For example, a plurality of oligonucleotides having up to about 100-bp nucleotides and a complementary region containing about 20 nucleotides at the terminus are chemical synthesized. Then, they may be used in combination and in an overlap elongation process (Reference Document 7) to perform total synthesis of a gene of interest.

A recombinant vector according to the present invention can be constructed by ligating (inserting) a gene containing the above-described nucleotide sequence into a suitable vector. A vector used in the present invention has no particular limitation as long as the vector can replicate in a host or a gene of interest can be integrated into a host genome by means of the vector. Examples include bacteriophages, plasmids, cosmids, and phagemids.

Examples of the plasmid DNA include *Actinomyces*-derived plasmids (e.g., pK4, pRK401, pRF31), *E. coli*-derived plasmids (e.g. pBR322, pBR325, pUC118, pUC119, pUC18), *Bacillus subtilis*-derived plasmids (e.g., pUB110, pTP5), and yeast-derived plasmids (e.g., YEp13, YEp24, YCp50). Examples of the phage DNA include λ phages (e.g., λgt10, λgt11, λZAP). Further, animal viruses such as a retrovirus or a vaccinia virus or insect virus vectors such as a baculovirus can be used.

In order to insert a gene into a vector, for example, a method is adopted in which purified DNA is first digested by a suitable restriction enzyme(s), is inserted into a restriction enzyme site(s) or a multi-cloning site of a suitable vector DNA, and is ligated to the vector. The gene should be cloned in the vector so as to express an improved protein according to the present invention. Here, a promoter and a gene nucleotide sequence as well as, as desired, a cis-element (e.g., an enhancer), a splicing signal, a poly-A tail signal, a selection marker, a ribosome binding sequence (SD sequence), a start codon, and/or a stop codon may be ligated to the vector according to the present invention. In addition, it is possible to add a tag sequence to easily purify a protein produced. Examples of the tag sequence that can be used include nucleotide sequences encoding known tags such as a His tag, a GST tag, and an MBP tag.

Whether or not the gene is inserted into the vector can be examined by using a known genetic engineering technology. For instance, the case of a plasmid vector, etc., can be examined by a procedure in which a competent cell is used for vector subcloning, DNA is extracted, a DNA sequencer is then used to check its nucleotide sequence. The similar procedure is applicable to other vectors as long as bacteria or other hosts can be used for subcloning. In addition, a vector is effectively selected by using a selection marker such as a drug resistance gene.

Transformants may be obtained by introducing a recombinant vector according to the present invention into a host cell so as to enable expression of an improved protein according to the present invention. A host used for transformation is not particularly limited if the host can express a protein or a polypeptide. Examples include bacteria (e.g., *Escherichia coli, Bacillus subtilis*), yeast, plant cells, animal cells (e.g., COS cells, CHO cells), and insect cells.

When a bacterium is used as a host, a recombinant vector should be able to self-replicate in the bacterium, and it is preferable that the vector includes a promoter, a ribosome binding sequence, a start codon, a nucleic acid encoding an improved protein according to the present invention, and a transcription termination sequence. Examples of the *Escherichia coli* include *Escherichia coli* DH5a. Examples of the *Bacillus* include *Bacillus subtilis*. A method for introducing a recombinant vector into a bacterium is not particularly limited if the method can introduce a DNA into a bacterium. Examples of the method include a method using a calcium ion and electroporation.

When the yeast is used as a host, for example, *Saccharomyces cerevisiae, Schizosaccharomyces pombe*, or another yeast may be employed. A method for introducing a recombinant vector into yeast is not particularly limited if the method can introduce a DNA into yeast. Examples of the method include electroporation, a spheroplast method, and a lithium acetate method.

When the animal cell is used as a host, a monkey cell COS-7, a Vero cell, a Chinese hamster ovary cell (CHO cell), a mouse L cell, a rat GH3, a human FL cell, or the like may be employed. Examples of a method for introducing a recombinant vector into an animal cell include electroporation, a calcium phosphate method, and lipofection.

When the insect cell is used as a host, Sf9 or another insect cell may be employed. Examples of a method for introducing a recombinant vector into an insect cell include a calcium phosphate method, lipofection, and electroporation.

Whether or not a gene is integrated into a host can be examined by a PCR method, Southern hybridization, Northern hybridization, or the like. For example, a DNA is prepared from a transformant, and DNA-specific primers are designed to carry out a PCR. Then, the resulting PCR amplification product is subjected to agarose gel electrophoresis, polyacrylamide gel electrophoresis, capillary electrophoresis, or the like. Subsequently, the amplification product is stained with, for example, ethidium bromide or a Syber-Green solution and is detected as a single band. This can verify that a cell has been transformed. In addition, a primer labeled in advance with, for example, a fluorescent dye can be used to carry out a PCR to detect its amplification product.

c. To Obtain Improved Protein by Culturing Transformant

When produced as a recombinant protein, an improved protein according to the present invention may be obtained by culturing the above-described transformant and by collecting the protein from the culture. The term "culture" means any of culture supernatant, cultured cells or microorganisms, and lysates of cells or microorganisms. Transformants according to the present invention may be cultured by a common procedure used for culturing their host.

Either a natural medium or a synthetic medium may be used as a medium for culturing a transformant obtained by using a microorganism such as *E. coli* or yeast as a host if the medium contains, for example, a carbon source, a nitrogen source, and inorganic salts, as utilized by the microorganism, to efficiently culture the transformant.

Examples of the carbon source include carbohydrates (e.g., glucose, fructose, sucrose, starch), organic acids (e.g., acetic acid, propionic acid), and alcohols (e.g., ethanol, propanol). Examples of the nitrogen source include ammonia, ammonium chloride, ammonium salts of inorganic or organic acids (e.g., ammonium sulfate, ammonium acetate, ammonium phosphate), other nitrogen-containing compounds, peptone, meat extracts, and corn steep liquors. Examples of the inorganic matter include potassium primary phosphate, potassium secondary phosphate, magnesium phosphate, magnesium sulfate, sodium chloride, ferrous sulfate, manganese sulfate, copper sulfate, and calcium carbonate. The culturing is carried out at 20 to 37° C. for 12 h to 3 days under aerobic conditions such as shaking culture or aerated and agitated culture.

When an improved protein according to the present invention is produced in microbial bodies or cells after culturing, the protein may be collected, for example, after homogenization (e.g., sonication, repeated freeze-thawing) so as to disrupt the microbial bodies or cells. In addition, when the protein is secreted from microbial bodies or cells, the resulting culture medium may be used as it is or is, for example, centrifuged to remove the microbial bodies or cells. Then, common biochemical processes used for isolating and purifying a protein are used singly or in combination, including ammonium sulfate precipitation, size-exclusion chromatography, ion exchange chromatography, and affinity chromatography. By doing so, an improved protein according to the present invention can be isolated and purified from the culture.

In addition, it is possible to use what is called a cell-free synthesis system using a mixture of only protein biosynthesis reaction-involving factors (e.g., enzymes, nucleic acids, ATP, amino acids). In this case, an improved protein according to the present invention can be synthesized from a vector without using viable cells (Reference Document 8). Then, the purification processes may be likewise used to isolate and purify the improved protein according to the present invention from a post-reaction mixed solution.

To check whether the purified/isolated improved protein according to the present invention is a protein consisting of an amino acid sequence of interest, a sample containing the protein is analyzed. Analysis methods may be used, including SDS-PAGE, Western blotting, mass spectroscopy, amino acid analysis, and analysis using an amino acid sequencer (Reference Document 9).

(2) To Produce Improved Protein by Using Another Technique

An improved protein according to the present invention may be produced using an organic chemistry technique (e.g., a solid peptide synthesis process). A process for producing a protein by using such a technique is well-known in the art and is briefly described below.

When a protein is chemically produced using a solid peptide synthesis process, an automatic synthesizer is preferably used to synthesize, on a resin, a protected polypeptide having an amino acid sequence of an improved protein according to the present invention while repeating a polycondensation reaction of activated amino acid derivatives. Next, this protected polypeptide is cleaved from the resin and, at the same time, a side chain protection group is cleaved. Regarding this cleavage reaction, it has been known that there is a suitable cocktail prepared in accordance with a type of resin or protection group and/or an amino acid composition (Reference Document 10). Subsequently, a crude protein is transferred from an organic solvent layer to an aqueous layer and a mutant protein of interest is then purified. Examples of the purification process that can be used include reverse-phase chromatography (Reference Document 10).

(Tests for Checking Performance of Improved Protein)

The following tests for checking performance may be conducted to select which of the improved proteins as so produced are good. Here, any of the improved proteins according to the present invention had good performance.

(1) Test for G-CSF Receptor-binding Activity

The G-CSF receptor-binding activity of an improved protein according to the present invention may be checked and evaluated using Western blotting, immunoprecipitation, pull-down assay, ELISA (Enzyme-Linked ImmunoSorbent Assay), surface plasmon resonance (SPR) spectroscopy, etc. Among them, the SPR spectroscopy enables real-time sequential observation of the interaction between label-free biomolecules. Accordingly, the SPR spectroscopy makes it possible to quantitatively evaluate a binding reaction of the improved protein from the kinetic viewpoint.

(2) Test for Activity of Improved Protein on Cells

The activity of an improved protein according to the present invention on cells can be evaluated using, as an index, a proliferation potential of a G-CSF-dependent culture cell line (NFS-60). The NFS-60 is a cell line exhibiting the G-CSF-dependent proliferation potential and a cell line generally used for biological activity assay for G-CSF including a standard G-CSF product produced by NIBSC. Hence, the cell line is suitable when the activity of the improved protein on cells is evaluated.

(3) Test for Thermostability of Improved Protein

The thermostability of an improved protein according to the present invention can be evaluated using circular dichroism (CD) spectroscopy, fluorescence spectroscopy, infrared spectroscopy, differential scanning calorimetry, residual activity after heating, etc. Among them, the CD spectroscopy is a spectroscopic analysis method that precisely reflects a change in the secondary structure of a protein. Because of this, it is possible to observe a temperature-dependent change in the conformation of the improved protein and to quantitatively evaluate the thermodynamical structural stability thereof.

(4) Test for Stability of Improved Protein Against Protease

The stability of an improved protein according to the present invention against a protease can be evaluated using, for example, a protocol in which a protease such as carboxypeptidase Y and the improved protein are mixed; and the amount of a degradation product caused by the reaction or the amount of a remaining unreacted molecule is analyzed over time by using SDS-PAGE, liquid chromatography, etc. Among them, the SDS-PAGE can be used to analyze a trace amount of a protein in a simple fashion, so that this method is suitable when the stability of the improved protein against a protease is evaluated.

(5) Test for In Vivo Stability of Improved Protein

The in vivo stability of an improved protein according to the present invention can be evaluated using, for example, a protocol in which the improved protein is intravenously injected into a rat; and the concentration of G-CSF present in blood is analyzed over time by using ELISA, SDS-PAGE, liquid chromatography, etc. Among them, the ELISA analysis can be used to quantify a trace amount of G-CSF in a sample containing serum components in a simple and accurate manner, so that the method is suitable when the in vivo stability is evaluated.

(6) Conformation Analysis of Improved Protein

The conformation of an improved protein according to the present invention can be evaluated using X-ray crystallography, nuclear magnetic resonance spectroscopy, etc. Among them, the X-ray crystallography can be used to analyze a high-resolution diffraction image and to precisely observe a local structure including the conformation of terminal regions that are subjected to cyclization, so that the method is suitable when the conformation of the improved protein is evaluated.

EXAMPLES

Example 1: To Design Improved G-CSFs (1) As used herein, a linear control G-CSF, which is a starting material for improvement, is defined as follows. Specifically, the linear control G-CSF is a linear polypeptide consisting of 175 amino acids set forth in SEQ ID NO: 1. When the amino acid sequence of the linear control G-CSF is compared with the amino acid sequence (SEQ ID NO: 14) of filgrastim, threonine at position 2 and cysteine at position 18 are replaced by alanine and serine, respectively. A previous report has demonstrated that these mutations do not affect the activity of G-CSF (Reference Document 3).

(2) In order to make a polypeptide of interest cyclic by using the catalytic function of inteins, a residue of at least one of the N-terminus and the C-terminus should be serine or cysteine. In addition, if the residue at the C-terminus is proline, it is known that the reaction fails to proceed. Here, as a mutant modified so as to make the inteins reaction proceed by introducing the minimum number of mutations, G-CSF(C177) (SEQ ID NO: 2) was produced by designing a sequence in which serine and glycine were added to the N-terminus and the C-terminus of the linear control G-CSF, respectively.

(3) Next, designed were G-CSFs, the terminal sequences of which were optimized for a cyclization reaction. First, human G-CSF three-dimensional structural coordinate data (PDB code: 2D9Q-A chain) was downloaded from the Protein Data Bank (PDB; rcsb.org/), an international database for the three-dimensional structures of proteins. Next, nonstructural regions that were disadvantageous for the cyclization reaction were selected and removed from amino acids positioned at the N-terminus and the C-terminus of G-CSF. According to the STRIDE, which is a secondary structure-determining algorithm provided at the PDB, an N-terminal region from glutamine at position 11 to serine at position 37 (corresponding to a region from position 12 to position 38 of the linear control G-CSF) forms a helix (helix A). Meanwhile, a C-terminal region from alanine at position 143 to leucine at position 171 (corresponding to a region from position 144 to position 172 of the linear control G-CSF) forms a helix structure (helix D) (FIG. 1). Then, 11 amino acids from methionine at position 1 to proline at position 11 and 3 amino acids from alanine at position 173 to proline at position 175 were deleted from the linear control G-CSF to give a sequence as a backbone suitable for cyclization.

Subsequently, the optimal length of a loop used to connect the N-terminus and the C-terminus was determined using the following procedure.

The high-resolution three-dimensional structures having a resolution of at least 2.5 Å and registered at the PDB were collected. Among the structures, the structure of a loop sandwiched between two helices was retrieved. Among the loop structures, retrieved were 57 loop structures in which 4 amino acids at each terminus (the total of 8 amino acids) of the backbone are structurally similar (i.e., the root mean square deviation of α-carbon is less than 1 Å) to 4 amino acids at the terminus of each helix (the total of 8 amino acids). The numbers of amino acids of such loop structures were set to references and were used for comparison. This comparison demonstrated that the number of the loop structure consisting of 2 amino acids was 13 (accounted for 22% of the total). Accordingly, it was determined that two amino acids were sufficient for the loop connecting the N-terminus and the C-terminus. An amino acid sequence containing serine and glycine as the loop sequence was added to give G-CSF(C163) (SEQ ID NO: 5), the smallest improved G-CSF suitable for the cyclization reaction.

On one hand, minimization of the loop region increases cyclization reaction efficiency. On the other hand, the minimization may cause distortion of the three-dimensional structure, thereby decreasing the stability. From this, it can be predicted that the number of amino acids, which number makes maximum the total of the increase in the cyclization reaction efficiency and the effect of stabilizing the structure, is present between those of G-CSF(C177) and G-CSF (C163). Specifically, G-CSF(C170) and G-CSF(C166) set forth in SEQ ID NOs: 3 and 4, respectively, are exemplified as the candidates.

Example 2: To Synthesize Linear Control G-CSF-Expression Plasmid (1) A chemically synthesized nucleic acid sequence (SEQ ID NO: 25) encoding the amino acid sequence (SEQ ID NO: 1) of the linear control G-CSF was purchased.

(2) As the chemically synthesized nucleic acid as a template, PCR amplification was carried out using two primers (SEQ ID NOs: 26 and 27). The resulting PCR product was purified and digested by restriction enzymes NcoI and BamHI. Next, an E. coli vector pET16b was digested by restriction enzymes NcoI and BamHI and a band at or near 5600 bp was excised and purified. The band was dephosphorylated using E. coli alkaline phosphatase. The two samples purified were ligated using T7 DNA ligase.

(3) E. coli DH5a was transformed with the resulting ligation product of (2) and was cultured on an LB plate medium containing 100 µg/ml of ampicillin. The resulting transformants were subjected to colony PCR and DNA sequencing (GE Healthcare Bioscience, BigDye Terminator v3.1) and were then selected. After that, a QIAprep Spin Miniprep kit (Qiagen) was used to extract a linear control G-CSF-expression plasmid.

Example 3: To Construct Inteins Vector (1) A synthetic gene was purchased having a nucleotide sequence (SEQ ID NO: 28) encoding the inteins sequence (a sequence containing, in sequence, SEQ ID NO: 15 and SEQ ID NO: 16) derived from *Nostoc punctiforme*.

(2) The synthetic gene of (1) was mixed with restriction enzymes NcoI and XhoI and was subjected to a cleavage reaction at 37° C. for 4 h. After gel electrophoresis, a band at or near 450 bp was excised and purified. Next, an E. coli vector pET16b was digested by NcoI and XhoI and a band at or near 5600 bp was excised and purified. The band was dephosphorylated using E. coli alkaline phosphatase. The two samples purified were ligated using T7 DNA ligase.

(3) E. coli DH5a was transformed with the resulting ligation product and was cultured on an LB plate medium containing 100 µg/ml of ampicillin. The resulting transformants were subjected to colony PCR and DNA sequencing (GE Healthcare Bioscience, BigDye Terminator v3.1) and were then selected. After that, a QIAprep Spin Miniprep kit (Qiagen) was used to extract an inteins-expression plasmid.

Example 4: To Synthesize G-CSF(C177)-Expression Plasmid

A nucleic acid (SEQ ID NO: 17) encoding the amino acid sequence of G-CSF(C177) was synthesized by PCR reaction using the linear control G-CSF-expression plasmid as a template and two single strand DNAs (SEQ ID NO: 29 and SEQ ID NO: 30) as primers. The resulting product was digested by restriction enzymes NheI and NdeI and was then purified. Next, the inteins-expression plasmid was digested by restriction enzymes NheI and NdeI and was then purified. The two samples purified were ligated using T7 DNA ligase. E. coli DH5a was transformed with the resulting ligation product and was cultured on an LB plate medium containing 1004 ml of ampicillin. The resulting transformants were subjected to colony PCR and DNA sequencing (GE Healthcare Bioscience, BigDye Terminator v3.1) and were then selected. After that, a QIAprep Spin Miniprep kit (Qiagen) was used to extract a G-CSF(C177)-expression plasmid.

Example 5: To Synthesize G-CSF(C163)-Expression Plasmid

A nucleic acid (SEQ ID NO: 20) encoding the amino acid sequence of G-CSF(C163) was synthesized by PCR reaction using the linear control G-CSF-expression plasmid as a template and two single strand DNAs (SEQ ID NO: 35 and SEQ ID NO: 36) as primers. The resulting product was digested by restriction enzymes NheI and NdeI and was then purified. Next, the inteins-expression plasmid was digested by restriction enzymes NheI and NdeI and was then purified. The two samples purified were ligated using T7 DNA ligase. E. coli DH5α was transformed with the resulting ligation product and was cultured on an LB plate medium containing 100 µg/ml of ampicillin. The resulting transformants were subjected to colony PCR and DNA sequencing (GE Healthcare Bioscience, BigDye Terminator v3.1) and were then selected. After that, a QIAprep Spin Miniprep kit (Qiagen) was used to extract a mutant G-CSF(C163)-expression plasmid.

Example 6: To Produce Linear Control G-CSF, and G-CSF(C177) and G-CSF(C163)

(1) E. coli BL21(DE3) (Novagen), which was used for expression, was transformed with the linear control G-CSF-expression plasmid. The resulting transformant was pre-cultured and was inoculated in an LB medium at 1 ml/200 ml and the mixture was cultured under shaking until O.D.$_{600}$=0.8 to 1.0. To express the linear control G-CSF, IPTG (0.4 mM) was added and the mixture was further cultured under shaking at 37° C. for 4 h.

(2) The bacteria collected were suspended in 10 ml of a lysis buffer. The lysis buffer is a PBS containing 1% (w/v) sodium deoxycholate (DOC), 1.2 kU/ml lysozyme, and 25 U/ml Benzonase. After the suspension, the lysate was stirred at room temperature for 15 min and was subjected to sonication for 2 min, followed by centrifugation at 4° C. for 10 min at 10,000×g. The supernatant was removed, and 20 ml of washing buffer 1 was added to the precipitate to be suspended. Washing buffer 1 contains 50 mM Tris-HCl pH 8.0 (25° C.), 5 mM EDTA, and 2% Tween20. The suspended sample was centrifuged to remove the supernatant. Then, 20 ml of washing buffer 2 was added to the precipitate to be suspended. Washing buffer 2 contains 50 mM Tris-HCl pH 8.0 (25° C.), 5 mM EDTA, and 1% (w/v) DOC. The suspended sample was centrifuged to remove the supernatant. Then, 20 ml of washing buffer 3 was added to the precipitate to be suspended. Washing buffer 3 contains 50 mM Tris-HCl pH 8.0 (25° C.), 5 mM EDTA, and 1 M NaCl. The suspended sample was centrifuged to remove the supernatant. Then, 10 ml of a solubilization buffer was added to the precipitate, and the mixture was stirred at room temperature for 18 h. The solubilization buffer contains 50 mM Tris-HCl pH 8.0 (25° C.), 5 mM EDTA, and 6 M guanidine hydrochloride. The solubilized sample was concentrated by size-exclusion filtration and the concentrate was added dropwise to the 10-fold volume of an ice-cold refolding buffer. Next, the mixture, as it was, was stirred at 4° C. for 18 h. The refolding buffer contains 100 mM Tris-HCl pH 8.0 (4° C.), 2 mM EDTA, 400 mM L-arginine, 1 mM reduced glutathione, and 0.1 mM oxidized glutathione. After that, the refolded sample was used as internal liquid and the 100-fold volume of 20 mM Tris-HCl pH 8.0 (4° C.) was used as external liquid to carry out dialysis (at 4° C. for 18 h). The sample was centrifuged to recover the supernatant, which was filtered with a 0.22-µm syringe filter and was subjected to dialysis using 20 mM Tris-HCl pH 8.0 (25° C.).

(3) The filter-sterilized dialysis internal liquid was injected into a HiTrap Q HP column (GE Healthcare Bioscience) of a liquid chromatography apparatus AKTApurifier (GE Healthcare Bioscience). Then, the linear control G-CSF was purified by anion exchange chromatography (a running buffer: 20 mM Tris-HCl pH 8.0 (25° C.); an elution buffer: 20 mM Tris-HCl pH 8.0 (25° C.) and 1 M NaCl). Further, the purified sample was injected into a Superdex75 10/300 GL column (GE Healthcare Bioscience) of the liquid chromatography apparatus AKTApurifier (GE Healthcare Bioscience). The sample was purified by size-exclusion chromatography (a running buffer: 20 mM Tris-HCl pH 8.0 (25° C.) and 150 mM NaCl). The purified sample was subjected to dialysis using PBS and was then stored at 4° C.

(4) G-CSF(C177) and G-CSF(C163) were likewise produced using the procedures (1), (2), and (3). In this regard, however, to isolate a linear molecule produced as a by-product of the inteins reaction, the following manipulations were added to the step of purifying G-CSF(C177). The sample purified by size-exclusion chromatography was concentrated by size-exclusion filtration, followed by dialysis using the 100-fold volume of 20 mM Tris-HCl pH 8.0 (25° C.). The filter-sterilized dialysis internal liquid was injected into a MonoQ column (GE Healthcare Bioscience) of a liquid chromatography apparatus AKTApurifier (GE Healthcare Bioscience). Then, the G-CSF(C177) was purified by anion exchange chromatography (a running buffer: 20 mM Tris-HCl pH 8.0 (25° C.); an elution buffer: 20 mM Tris-HCl pH 8.0 (25° C.) and 1 M NaCl). When the amount of G-CSF(C177) added to the above-described column was 20 µg or less, a cyclized main product and a linear by-product were separated as 2 independent peaks. The purified sample of interest was subjected to dialysis using PBS and was then stored at 4° C.

Example 7: To Measure Cyclization Efficiency by Using SDS-PAGE

In this example, the purity of each G-CSF after purification was evaluated by using SDS-PAGE.

An aqueous solution containing each purified G-CSF at a concentration of about 50 µM was prepared and was subjected to SDS-PAGE (4 to 20% precast gels (Bio-Rad), at 200 V for 30 min). Then, an Oriole® Fluorescent Gel Stain kit (Bio-Rad) was used to detect a band, and the purity of each G-CSF was determined. The results showed that the linear control G-CSF and G-CSF(C163) were each detected as a major band of any of the samples measured and that the degree of purification was sufficient. The G-CSF(C177) sample after the size-exclusion chromatography contained about 30% of a linear molecule and the purity of the cyclized product was demonstrated to be 70% or less. However, the purity after the final purification using a MonoQ column was demonstrated to be 95% or higher (FIG. 3 and Table 1).
Table 1. The cyclization efficiency and the function and stability of each modified cyclized G-CSF were compared.

TABLE 1

| | Cyclization efficiency (%) | G-CSF receptor-binding activity KD (nM) | Activity on cells EC50 (pg/ml) | Thermo-stability Tm (° C.) | Protease resistance t0.5 (hours) | Metabolic half-life t0.5 (hours) |
|---|---|---|---|---|---|---|
| filgrastim | — | 0.19* | 103 | N.A. | 2.0 | N.A. |
| Linear control G-CSF | — | 0.43 | 82.3 | 56.5 | 1.7 | 0.95 |
| G-CSF(C177) | 63.6 | 0.57 | 60.7 | 66.2 | 230 | 1.13 |
| G-CSF(C163) | 100 | 0.57 | 80.6 | 58.3 | 11 | 1.05 |

*The value reported (by Feng Y et al., 1999, Biochemistry) was cited.

Example 8: To Measure G-CSF Receptor-Binding Activity by Using Surface Plasmon Resonance Spectroscopy As described below, surface plasmon resonance (SPR) spectroscopy was used to evaluate the receptor-binding activity of each of the linear control G-CSF, G-CSF(C177), and G-CSF(C163).

Note that SPR spectroscopy is recognized as an excellent method in which the specific interaction between biopolymers is measured over time and the reaction can be quantitatively interpreted from the kinetic viewpoint.

First, Protein G was immobilized on a flow cell of a sensor chip CM5 (GE Health care) by using a maleimide coupling reaction. Next, a running buffer HBS-P (10 mM HEPES pH 7.4, 150 mM NaCl, and 0.05% v/v Surfactant P20) in which an Fc-fusion G-CSF receptor had been dissolved was added to immobilize the receptor on the chip. The SPR measurement was carried out using Biacore T100 (Biacore) and the reaction temperature was 25° C. A 2-fold dilution series from 1.25 nM to 20 nM of the sample solution was prepared, and a single kinetic mode was used for measurement and analysis.

The observation results were analyzed using BIAevaluation version 4.1 to calculate a dissociation constant. The results demonstrated that the dissociation constant between G-CSF(C177) or G-CSF(C163) and the G-CSF receptor was substantially the same value as of the linear control G-CSF, indicating that the affinity remained the same (FIG. 4 and Table 1).

Example 9: To Measure Activity on Cells

In this Example, evaluated was the activity of each of filgrastim, the linear control G-CSF, G-CSF(C177), and G-CSF(C163) on cells.

A cell line NFS-60, which exhibits G-CSF-dependent growth, was maintained under conditions at 37° C. and 5% $CO_2$ in RPMI1640 culture medium containing 10 ng/ml rhG-CSF and 10% FBS. The cells in a logarithmic growth phase were prepared at $2 \times 10^5$ cells/mL in 10% FBS-containing (culture-use rhG-CSF-free) RPMI1640 culture medium, and were then used for experiments. A 5-fold dilution series from 3 nM to 192 fM of the linear control G-CSF, G-CSF(C177), or G-CSF(C163) was prepared using 10% FBS-containing RPMI1640 culture medium. Equal volumes of the cell solution and each G-CSF solution were mixed and the mixture was cultured under conditions at 37° C. and 5% $CO_2$ for 48 h. Then, a cell counting kit-8 (DOJINDO LABORATORIES) was used to count the number of cells.

As a growth-stimulating activity on NFS-60 cells, the G-CSF activity of each of the linear control G-CSF, G-CSF (C177), and G-CSF(C163) was evaluated by calculating 50% effective concentration (EC50) as obtained by fitting a logistic curve to the activity data. The average of the vehicle control (VC) was subtracted from absorbance data obtained using each sample at each concentration. Then, the resulting value was divided by the average of values of the reference at the maximum activity concentration to calculate a relative activity (%) for each plate. The maximum value was set to 100%, and a logistic formula (Hill equation) was fit to the data to calculate an EC50 value.

The results demonstrated that G-CSF(C177) and G-CSF (C163) exhibited substantially the same activity on cells as of filgrastim or the linear control G-CSF(FIG. 5 and Table 1).

Example 10: To Determine Thermostability by Using Circular Dichroism Spectroscopy In this Example, evaluated was the thermostability of each of the linear control G-CSF, G-CSF(C177), and G-CSF (C163). Circular dichroism (CD) spectroscopy is known to be a spectroscopic analysis method that precisely reflects a change in the secondary structure of a protein. The method can reveal at which temperature a sample is denatured by measuring a molar ellipticity, which is represented by the intensity of a CD spectrum, while the temperature of the sample is changed.

An aqueous solution (10 mM HEPES buffer, pH 7.4, and 150 mM sodium chloride) containing the linear control G-CSF, G-CSF(C177), or G-CSF(C163) at a concentration of 5 μM was prepared. This sample solution was injected into a cylindrical cell (with a cell length of 0.2 cm), and a circular dichroism spectrophotometer model J805 (JASCO Corporation) was used for measurement.

While the measurement wavelength at a temperature of 10° C. was shifted from 260 nm to 200 nm, a circular dichroism spectrum was obtained. The results showed that the linear control G-CSF, G-CSF(C177), and G-CSF(C163) had substantially the same secondary structure. The same samples were heated to 80° C. and then cooled from 80° C. to 10° C. After that, a circular dichroism spectrum was remeasured. The molar ellipticity, however, was not recovered, indicating the occurrence of irreversible heat denaturation.

Next, while the temperature was raised from 10° C. to 80° C. at a rate of 1° C. per min, their circular dichroism at a wavelength of 222 nm was scanned and determined. The resulting heat-fusing curve was analyzed using a theoretical formula of a two-state phase transition model (Reference Document 11). This analysis determined a denaturation temperature $T_m$ and a denaturation enthalpy change $\Delta H_m$ at the $T_m$. The results revealed that the thermostability of each of G-CSF(C177) and G-CSF(C163) was increased by 9.7° C. and 1.8° C., respectively, when compared with that of the linear control G-CSF (FIG. 6 and Table 1).

Example 11: Protease Resistance Test

In this Example, the protease resistance of each of filgrastim, the linear control G-CSF, G-CSF(C177), and G-CSF(C163) was evaluated.

Carboxypeptidase Y and each G-CSF were mixed, and the proportion of an unreacted G-CSF was quantified using SDS-PAGE. Carboxypeptidase Y is an enzyme that catalyzes the cleavage of an amino acid from the C-terminus of a protein and exhibits low substrate specificity and sequence specificity during the reaction. Because of this, carboxypeptidase Y is effective in comprehensively evaluating protease resistance.

The linear control G-CSF, G-CSF(C177), or G-CSF (C163), isolated and purified, and carboxypeptidase Y were diluted and mixed in 100 mM acetate buffer (pH 6.5) at a final concentration of 10 µg/ml and 1 µg/ml, respectively. The reaction was carried out at 37° C. for 0, 60, 120, 180, and 240 min, and 10 µl of each sample was collected. Each sample was subjected to SDS-PAGE (4 to 20% precast gels (Bio-Rad), at 200 V for 30 min), and an Oriole® Fluorescent Gel Stain kit (Bio-Rad) was used to detect a band. An imaging system (ChemiDoc™, BioRad) and image-analyzing software (QuantityOne™, BioRad) were used to detect the band and quantify its image density. The result at 0 min was set to 100%, and the level of the remaining band was scored. The carboxypeptidase Y-mediated digestion reaction was assumed to be a pseudo-first-order reaction to calculate a half-life (FIG. 7 and Table 1). The results showed that G-CSF(C177) and G-CSF(C163) had markedly higher protease resistance than the linear control G-CSF.

Example 12: Test for Measuring Metabolic Half-life

In this Example, evaluated was the pharmacokinetics of each of the linear control G-CSF, G-CSF(C177), and G-CSF (C163).

A single dose of each sample was administered at 100 µg protein/kg to a tail vein of each 7-week-old male Sprague-Dawley rat. Then, 20 min, 1.5 h, 3 h, 4.5 h, 6 h, and 24 h after the administration, 100 µl of blood was taken via a tail vein. Each blood sample was fractionated by centrifugation and the serum concentration of the remaining G-CSF was quantified using a G-CSF Human ELISA kit (Abcam®).

The results showed that the linear control G-CSF, G-CSF (C177), and G-CSF(C163) had a calculated metabolic half-life of 0.95 h, 1.13 h, and 1.05 h, respectively, indicating that G-CSF(C177) and G-CSF(C163) had a decrease in in vivo clearance efficiency (Table 1).

Example 13: X-Ray Crystallography

In this Example, a single crystal of each improved protein was created and its three-dimensional structure was determined by X-ray crystallography. X-ray crystallography is a technique in which the high-resolution structure of a protein can be observed and can be used to check whether or not its cyclization occurs definitely and whether or not the cyclization causes a change in its receptor-binding interface.

Regarding G-CSF(C177), a mother liquor containing 200 mM $Li_2SO_4$, 100 mM Tris-HCl (pH 8.4), and 20% (w/v) PEG 4000 was used for crystallization to give a columnar single crystal. This crystal was used to obtain diffraction data with a resolution of 3.0 Å. Meanwhile, regarding G-CSF(C163), a mother liquor containing 0.4 M ammonium phosphate was used for crystallization to give a regular octahedral single crystal. This crystal was used to obtain diffraction data with a resolution of 1.65 Å. These two different diffraction data were used to construct each three-dimensional structure model.

First, it was verified that the N-terminal region and the C-terminal region of each were made cyclic. With respect to each of G-CSF(C177) and G-CSF(C163), obtained were electron density maps elucidating that the serine residue at the N-terminus and the glycine residue at the C-terminus were bonded (FIG. 8). The three-dimensional structure of each of G-CSF(C177) and G-CSF(C163) was superimposed on the known three-dimensional structure (PDB code: 2DQ9-A chain) of the linear control G-CSF. Then, whether the introduced mutations did not affect the G-CSF receptor-binding interface was checked.

There are two separate interaction interfaces between G-CSF and its receptor (site II and site III). A report said that each interface requires 8 amino acids for the binding (Reference Document 12). The positions of these 16 amino acids were compared among the linear control G-CSF, G-CSF (C177), and G-CSF(C163). The results showed that the distances between the corresponding α-carbons of the G-CSFs were each less than 3 Å, indicating no difference in their three-dimensional structures (Table 2).

Table 2. Comparison of the position of α-carbon of each amino acid used to form the G-CSF receptor-binding interface between the known three-dimensional structure (PDB code: 2D9Q-A chain) of human G-CSF and the three-dimensional structure of each of G-CSF(C177) and G-CSF (C163) by using X-ray crystallography.

TABLE 2

| | Known structure of G-CSF (2D9Q A chain) | G-CSF(C177) | | G-CSF(C163) | |
|---|---|---|---|---|---|
| | | Distance (Å) | (Corresponding amino acid) | Distance (Å) | (Corresponding amino acid) |
| site II | Lys-16 | 0.49 | (Lys-18) | 1.00 | (Lys-7) |
| | Glu-19 | 0.38 | (Glu-21) | 0.73 | (Glu-10) |
| | Gln-20 | 0.10 | (Gln-22) | 0.35 | (Gln-11) |
| | Arg-22 | 0.86 | (Arg-24) | 0.44 | (Arg-13) |
| | Lys-23 | 0.34 | (Lys-25) | 0.47 | (Lys-14) |
| | Leu-108 | 0.76 | (Leu-110) | 0.95 | (Leu-99) |
| | Asp-109 | 0.47 | (Asp-111) | 0.77 | (Asp-100) |
| | Asp-112 | 0.76 | (Asp-114) | 1.36 | (Asp-103) |
| site III | Tyr-39 | 0.65 | (Tyr-41) | 0.27 | (Tyr-30) |
| | Leu-41 | 0.30 | (Leu-43) | 0.33 | (Leu-32) |
| | Glu-46 | 1.44 | (Glu-48) | 1.37 | (Glu-37) |
| | Val-48 | 1.16 | (Val-50) | 1.74 | (Val-39) |
| | Leu-49 | 1.29 | (Leu-51) | 2.39 | (Leu-40) |
| | Ser-53 | 0.39 | (Ser-55) | 2.09 | (Ser-44) |
| | Phe-144 | 0.65 | (Phe-146) | 0.30 | (Phe-135) |
| | Arg-147 | 0.71 | (Arg-149) | 0.44 | (Arg-138) |

Example 14: To Improve Loop Length

In Example 1, the protein conformation models registered in the database (PDB) were also compared to the structure of G-CSF. As a result, 9 similar conformation models having the structure of a loop consisting of 9 amino acids were discovered (accounted for 16% of the total). Likewise, 15 similar conformation models having the structure of a loop consisting of 5 amino acids were found (accounted for 26% of the total). Then, two different modified G-CSFs were designed and produced such that corresponding seven or three amino acids of the amino acid sequence of the linear control G-CSF were maintained as much as possible, except for the serine at the N-terminus and the glycine at the C-terminus. Specifically, N-terminal 4 amino acid residues and C-terminal 3 amino acid residues of the amino acid sequence (SEQ ID NO: 1) of the linear control G-CSF were deleted; serine was added to the N-terminus and glycine was added to the C-terminus to give an engineered sequence (SEQ ID NO: 3); and split inteins were used to produce G-CSF(C170). Likewise, N-terminal 8 amino acid residues and C-terminal 3 amino acid residues of the amino acid sequence (SEQ ID NO: 1) of the linear control G-CSF were deleted; serine was added to the N-terminus and glycine was added to the C-terminus to give an engineered sequence (SEQ ID NO: 4); and split inteins were used to produce G-CSF(C166).

Example 15: To Synthesize G-CSF(C170)-Expression Plasmid

A nucleic acid (SEQ ID NO: 18) encoding the amino acid sequence of G-CSF(C170) was synthesized by PCR reaction using the linear control G-CSF-expression plasmid as a template and two single strand DNAs (SEQ ID NO: 31 and SEQ ID NO: 32) as primers. The resulting product was digested by restriction enzymes NheI and NdeI and was then purified. Next, the inteins-expression plasmid was digested by restriction enzymes NheI and NdeI and was then purified. The two samples purified were ligated using T7 DNA ligase. *E. coli* DH5α was transformed with the resulting ligation product and was cultured on an LB plate medium containing 100 μg/ml of ampicillin. The resulting transformants were subjected to colony PCR and DNA sequencing (GE Healthcare Bioscience, BigDye Terminator v3.1) and were then selected. After that, a QIAprep Spin Miniprep kit (Qiagen) was used to extract a G-CSF(C170)-expression plasmid.

Example 16: To Synthesize G-CSF(C166)-Expression Plasmid

A nucleic acid (SEQ ID NO: 19) encoding the amino acid sequence of G-CSF(C166) was synthesized by PCR reaction using the linear control G-CSF-expression plasmid as a template and two single strand DNAs (SEQ ID NO: 33 and SEQ ID NO: 34) as primers. The resulting product was digested by restriction enzymes NheI and NdeI and was then purified. Next, the inteins-expression plasmid was digested by restriction enzymes NheI and NdeI and was then purified. The two samples purified were ligated using T7 DNA ligase. *E. coli* DH5α was transformed with the resulting ligation product and was cultured on an LB plate medium containing 100 μg/ml of ampicillin. The resulting transformants were subjected to colony PCR and DNA sequencing (GE Healthcare Bioscience, BigDye Terminator v3.1) and were then selected. After that, a QIAprep Spin Miniprep kit (Qiagen) was used to extract a mutant G-CSF(C166)-expression plasmid.

Example 17: To Produce G-CSF(C170) and G-CSF(C166)

(1) *E. coli* BL21(DE3) (Novagen), which was used for expression, was transformed with the G-CSF(C170)-expression plasmid or the G-CSF(C166)-expression plasmid. The resulting transformant pre-cultured was inoculated in an LB medium at 1 ml/200 ml and the mixture was cultured under shaking until O.D.$_{600}$=0.8 to 1.0. To express the linear control G-CSF, IPTG (0.4 mM) was added and the mixture was further cultured under shaking at 37° C. for 4 h.

(2) The bacteria collected were suspended in 10 ml of a lysis buffer. The lysis buffer is a PBS containing 1% (w/v) sodium deoxycholate (DOC), 1.2 kU/ml lysozyme, and 25 U/ml Benzonase. After the suspension, the mixture was stirred at room temperature for 15 min and was subjected to sonication for 2 min. Then, the mixture was centrifuged at 4° C. for 10 at 10,000×g. The supernatant was removed, and 20 ml of washing buffer 1 was added to the precipitate to be suspended. Washing buffer 1 contains 50 mM Tris-HCl pH 8.0 (25° C.), 5 mM EDTA, and 2% Tween20. The suspended sample was centrifuged to remove the supernatant. Then, 20 ml of washing buffer 2 was added to the precipitate to be suspended. Washing buffer 2 contains 50 mM Tris-HCl pH 8.0 (25° C.), 5 mM EDTA, and 1% (w/v) DOC. The suspended sample was centrifuged to remove the supernatant. Then, 20 ml of washing buffer 3 was added to the precipitate to be suspended. Washing buffer 3 contains 50 mM Tris-HCl pH 8.0 (25° C.), 5 mM EDTA, and 1 M NaCl. The suspended sample was centrifuged to remove the supernatant. Then, 10 ml of a solubilization buffer was added to the precipitate, and the mixture was stirred at room temperature for 18 h. The solubilization buffer contains 50 mM Tris-HCl pH 8.0 (25° C.), 5 mM EDTA, and 6 M guanidine hydrochloride. The solubilized sample was concentrated by size-exclusion filtration and the concentrate was added dropwise to the 10-fold volume of an ice-cold refolding buffer. Next, the mixture, as it was, was stirred at 4° C. for 18 h. The refolding buffer contains 100 mM Tris-HCl pH 8.0 (4° C.), 2 mM EDTA, 400 mM L-arginine, 1 mM reduced glutathione, and 0.1 mM oxidized glutathione. After that, the refolded sample was used as internal liquid and the 100-fold volume of 20 mM Tris-HCl pH 8.0 (4° C.) was used as external liquid to carry out dialysis (at 4° C. for 18 h). The sample was centrifuged to recover the supernatant, which was filtered with a 0.22-μm syringe filter and was subjected to dialysis using 20 mM Tris-HCl pH 8.0 (25° C.).

(3) The filter-sterilized dialysis internal liquid was injected into a HiTrap Q HP column (GE Healthcare Bioscience) of a liquid chromatography apparatus AKTApurifier (GE Healthcare Bioscience). Then, each G-CSF was purified by anion exchange chromatography (a running buffer: 20 mM Tris-HCl pH 8.0 (25° C.); an elution buffer: 20 mM Tris-HCl pH 8.0 (25° C.) and 1 M NaCl). Further, each purified sample was injected into a Superdex75 10/300 GL column (GE Healthcare Bioscience) of the liquid chromatography apparatus AKTApurifier (GE Healthcare Bioscience). Each sample was purified by size-exclusion chromatography (a running buffer: 20 mM Tris-HCl pH 8.0 (25° C.) and 150 mM NaCl). Each sample purified by size-exclusion chromatography was concentrated by size-exclusion filtration, followed by dialysis using the 100-fold volume of 20 mM Tris-HCl pH 8.0 (25° C.). The filter-sterilized dialysis internal liquid was injected into a MonoQ column (GE Healthcare Bioscience) of the liquid chromatography apparatus AKTApurifier (GE Healthcare Bioscience). Then, each G-CSF was purified by anion exchange chromatography (a running buffer: 20 mM Tris-HCl pH 8.0 (25° C.); an elution buffer: 20 mM Tris-HCl pH 8.0 (25° C.) and 1 M NaCl). Each purified sample was subjected to dialysis using PBS and was then stored at 4° C.

Example 18: To Measure Cyclization Efficiency by Using SDS-PAGE

In this example, the purity of each G-CSF after purification was evaluated by using SDS-PAGE.

An aqueous solution containing each purified G-CSF at a concentration of about 50 μM was prepared and was subjected to SDS-PAGE (4 to 20% gels (Bio-Rad), at 200 V for 30 min). Then, an Oriole® Fluorescent Gel Stain kit (Bio-Rad) was used to detect a band, and the purity of each G-CSF was determined. The results showed that the G-CSF (C170) and G-CSF(C166) were each detected as a major band of any of the samples measured and that the degree of purification was sufficient. Each sample after the size-exclusion chromatography was fractionated using a MonoQ column. G-CSF(C170) appeared as a single peak and no linear molecule was observed. By contrast, regarding G-CSF (C166), 4% of a linear molecule was observed in terms of a peak area (Table 3).

Table 3. The cyclization efficiency and the function and stability of each of G-CSF(C170) and G-CSF(C166) among the modified cyclized G-CSFs were compared to those of the linear control G-CSF.

TABLE 3

| | Cyclization efficiency (%) | G-CSF receptor-binding activity KD (nM) | Thermo-stability Tm (° C.) | Protease resistance t0.5 (hours) |
|---|---|---|---|---|
| filgrastim | — | 0.27 | N.A. | 2.0* |
| Linear control G-CSF | — | 0.08 | 56.5 | 1.7* |
| G-CSF(C177) | 63.6* | 0.06 | 62.1 | 230* |
| G-CSF(C170) | 100 | 0.05 | 64.1 | 10 |
| G-CSF(C166) | 96.0 | 0.06 | 69.1 | ** |
| G-CSF(C163) | 100* | 0.10 | 58.2 | 11* |

*The analysis values in Table 1 were used.
**No degradation was observed during the reaction.

Example 19: To Measure G-CSF Receptor-Binding Activity by Using Surface Plasmon Resonance Spectroscopy As described below, surface plasmon resonance (SPR) spectroscopy was used to evaluate the receptor-binding activity of each of G-CSF(C170) and G-CSF(C166)

Note that SPR spectroscopy is recognized as an excellent method in which the specific interaction between biopolymers is measured over time and the reaction can be quantitatively interpreted from the kinetic viewpoint.

First, commercially available Protein A (Nacalai Tesque, Inc.) was immobilized on a flow cell of a sensor chip CM5 (GE Health care) by using an amine coupling reaction. Next, a running buffer HBS-P (10 mM HEPES pH 7.4, 150 mM NaCl, and 0.05% v/v Surfactant P20) in which an Fc-fusion G-CSF receptor had been dissolved was added to immobilize the receptor on the chip. The SPR measurement was carried out using Biacore T200 (Biacore) and the reaction temperature was 25° C. A 2-fold dilution series from 1.25 nM to 20 nM of the sample solution was prepared, and a single kinetic mode was used for measurement and analysis. When compared with Example 8, this Example had improvements such as use of Biacore T200, which has higher sensitivity than Biacore T100, and use of commercially available Protein A. The improvements helped increase the sensitivity and reproducibility of measurement. Then, the linear G-CSF, G-CSF(C177), and G-CSF(C163) as measured in Example 8 were remeasured and the resulting analysis values were used for comparison.

The observation results were analyzed using BIAevaluation version 4.1 to calculate a dissociation constant. The results demonstrated that the dissociation constant between G-CSF(C170) or G-CSF(C166) and the G-CSF receptor was substantially the same value as of the linear control G-CSF, indicating that the affinity remained the same (FIG. 10 and Table 3).

Example 20: To Determine Thermostability by Using Circular Dichroism Spectroscopy In this Example, evaluated was the thermostability of each of G-CSF(C170) and G-CSF(C166). Circular dichroism (CD) spectroscopy is known to be a spectroscopic analysis method that precisely reflects a change in the secondary structure of a protein. The method can reveal at which temperature a sample is denatured by measuring a molar ellipticity, which is represented by the intensity of a CD spectrum, while the temperature of the sample is changed.

An aqueous solution (10 mM HEPES buffer, pH 7.4, and 150 mM sodium chloride) containing G-CSF(C170) or G-CSF(C166) at a concentration of 5 μM was prepared. This sample solution was injected into a cylindrical cell (with a cell length of 0.2 cm), and a circular dichroism spectrophotometer model J805 (JASCO Corporation) was used for measurement.

While the measurement wavelength at a temperature of 10° C. was shifted from 260 nm to 200 nm, a circular dichroism spectrum was obtained. The results showed that G-CSF(C170) and G-CSF(C166) had substantially the same secondary structure. The same samples were heated to 90° C. and then cooled from 90° C. to 10° C. After that, a circular dichroism spectrum was remeasured. The molar ellipticity, however, was not recovered, indicating the occurrence of irreversible heat denaturation.

Next, while the temperature was raised from 10° C. to 90° C. at a rate of 1° C. per min, their circular dichroism at a wavelength of 222 nm was scanned and determined. The resulting heat-fusing curve was analyzed using a theoretical formula of a two-state phase transition model (Reference Document 11). Then, the degeneration temperature $T_m$ was determined. At the time of curve fitting, a heat capacity change due to the denaturation was assumed and fixed to $\Delta Cp = 7.5 \text{ kJ} \cdot \text{mol}^{-1} \cdot \text{K}^{-1}$. When compared with Example 10, this Example was carried out by measuring thermal melting up to a higher temperature and by using a value representing the fixed heat capacity change, resulting in higher reproducibility. G-CSF(C177) was remeasured and re-analyzed under the same conditions. In addition, the linear control G-CSF and G-CSF(C163) were re-analyzed. The resulting analysis values were used for comparison.

The results revealed that the thermostability of each of G-CSF(C170) and G-CSF(C166) was increased by 7.6° C. and 12.6° C., respectively, when compared with that of the linear control G-CSF (FIG. 11 and Table 3). The results also revealed that the thermostability of each of G-CSF(C177) and G-CSF(C163) was increased by 5.6° C. and 1.7° C., respectively, when compared with that of the linear control G-CSF. Collectively, in terms of the thermostability, G-CSF (C166) was the most stable modified molecule.

Example 21: Protease Resistance Test

In this Example, the protease resistance of each of G-CSF (C170) and G-CSF(C166) was evaluated.

Carboxypeptidase Y and each G-CSF were mixed, and the proportion of an unreacted G-CSF was quantified using SDS-PAGE. Carboxypeptidase Y is an enzyme that catalyzes the cleavage of an amino acid from the C-terminus of a protein and exhibits low substrate specificity and sequence specificity during the reaction. Because of this, carboxypeptidase Y is effective in comprehensively evaluating protease resistance.

The G-CSF(C170) or G-CSF(C166), isolated and purified, and carboxypeptidase Y were diluted and mixed in 100 mM acetate buffer (pH 6.5) at a final concentration of 10 µg/ml and 1 µg/ml, respectively. The reaction was carried out at 37° C. for 0, 60, 120, 180, and 240 min, and 10 µl of each sample was collected. Each sample was subjected to SDS-PAGE (4 to 20% precast gels (Bio-Rad), at 200 V for 30 min), and an Oriole® Fluorescent Gel Stain kit (Bio-Rad) was used to detect a band. An imaging system (ChemiDoc™, BioRad) and image-analyzing software (QuantityOne™, BioRad) were used to detect the band and quantify its image density. The result at 0 min was set to 100%, and the level of the remaining band was scored. The carboxypeptidase Y-mediated digestion reaction was assumed to be a pseudo-first-order reaction to calculate a half-life (FIG. 12 and Table 3). The results showed that G-CSF(C170) and G-CSF(C166) had markedly higher protease resistance than the linear control G-CSF.

Note that the present application further relates to the following inventions.

<1> A method for producing a cyclized mutant protein with biological properties not less than those of an original protein and with stability higher than that of the original protein by modifying, through the following steps (a) and (b) and/or steps (c) to (f), the original protein with a specific three-dimensional structure, the method comprising the steps of:

(a) adding, to an N-terminus and/or an C-terminus of an amino acid sequence of the original protein, residue(s) that enables formation of a peptide bond therebetween by using a trans-splicing reaction using split inteins, provided that when amino acid residues at the N-terminus and the C-terminus of the amino acid sequence of the original protein are residues that enable the formation of a peptide bond, the amino acid residues may remain intact, and (b) linking the N-terminus and the C-terminus by using the trans-splicing reaction using the split inteins to make a polypeptide main chain cyclic; and if sufficient cyclization efficiency is not achieved after steps (a) and (b), (c) determining N-terminal and C-terminal secondary structure-free regions on a basis of conformational information about the original protein and deleting or mutating the regions, (d) screening a known protein database for a structure of a loop connecting secondary structures similar to N-terminal and C-terminal secondary structures of a protein obtained after step (c) and determining a suitable length of the loop, (e) adding, to an N-terminus and a C-terminus of the protein obtained after step (c), amino acid residues or amino acid sequences used to form the structure of the loop, with the suitable length, that connects the N-terminus and the C-terminus after cyclization, and (f) linking the N-terminus and the C-terminus by means of a chemical or biological technique to make the polypeptide main chain cyclic.

<2> The method for producing a cyclized mutant protein according to item<1>, wherein the polypeptide main chain cyclization of step (f) uses a trans-splicing reaction mediated by split inteins.

<3> The method for producing a cyclized mutant protein according to item<1> or <2>, wherein the original protein with a specific three-dimensional structure is a cytokine with a helix bundle structure and the biological properties of the original protein involve affinity for a receptor.

<4> A cyclized mutant protein produced using the production method according to any one of items<1> to <3>.

<5> The cyclized mutant protein according to item<4>, wherein the original cytokine is granulocyte colony-stimulating factor (G-CSF).

<6> The cyclized mutant protein according to item<5>, wherein the original cytokine is a granulocyte colony-stimulating factor (G-CSF) consisting of an amino acid sequence set forth in SEQ ID NO: 1.

<7> The cyclized mutant protein according to item<6>, wherein the protein consists of an amino acid sequence in which 0 to 11 amino acid residues are deleted from an N-terminus and 0 to 3 amino acid residues are deleted from a C-terminus of the amino acid sequence set forth in SEQ ID NO: 1; a serine residue or a cysteine residue is added to an N-terminus and/or a C-terminus after the deletion; and an amino acid residue other than proline is added to the C-terminus.

<8> The cyclized mutant protein according to item<7>, wherein the protein consists of a cyclized amino acid sequence set forth in any one of SEQ ID NOs: 6 to 9.

<9> A linear mutant protein is designed so as to produce, in accordance with the method according to any one of items<1> to <3>, the cyclized mutant protein according to item<8> and consisting of an amino acid sequence set forth in any one of SEQ ID NOs: 2 to 5.

<10> A linear mutant protein is designed so as to produce, in accordance with the method according to any one of items<1> to <3>, the mutant protein according to item<8> by using, as split inteins, DnaE-C(C-intein) and DnaE-N(N-intein) of DnaE derived from *Nostoc punctiforme* and consisting of an amino acid sequence set forth in any one of SEQ ID NOs: 10 to 13.

<11> A nucleic acid comprising a nucleotide sequence encoding an amino acid sequence of the mutant protein according to any one of items<4> to <10>.

<12> A recombinant vector comprising the nucleic acid according to item<11>.

<13> A transformant comprising the recombinant vector according to item<12>.

<14> A method for producing the mutant protein according to any one of items<4> to <10>, comprising using the transformant according to item<13>.

<15> A pharmaceutical composition comprising, as an active ingredient, the mutant protein according to any one of items<5> to <9>.

<16> A pharmaceutical composition for treatment of neutropenia, comprising, as an active ingredient, the mutant protein according to any one of items<5> to <9>.

LIST OF REFERENCE DOCUMENTS

Reference Document 1; B. I. Lord, L. B. Woolford, and G. Molineux, Clin. Cancer Res., 2001, 7, 2085-90.

Reference Document 2; M. W. Popp, S. K. Dougan, T. Y. Chuang, E. Spooner, and H. L. Ploegh, Proc. Natl. Acad. Sci. U.S.A, 2011, 108, 3169-74

Reference Document 3; T. Kuga, Y. Komatsu, M. Yamasaki, S. Sekine, H. Miyaji, T. Nishi, M. Sato, Y. Yokoo, M. Asano, M. Okabe, M. Morimoto, and S. Itoh, Biochem. Biophys. Res. Commun., 1989, 159, 103-111.

Reference Document 4; W. Kabsch and C. Sander, Biopolymers, 1983, 22, 2577-637.

Reference Document 5; D. Frishman and P. Argos, Proteins, 1995, 23, 566-79.

Reference Document 6; C. P. Scott, E. Abel-Santos, M. Wall, D. C. Wahnon, and S. J. Benkovic, Proc. Natl. Acad. Sci., 1999, 96, 13638-13643.

Reference Document 7; R. M. Horton, H. D. Hunt, S. N. Ho, J. K. Pullen, and L. R. Pease, Gene, 1989, 77, 61-8.

Reference Document 8: OKADA, Masato and MIYAZAKI, Kaori (2004) "Tanpakushitsu Jikken Noto (Notes on Protein Experiments)" (I), YODOSHA CO., LTD.

Reference Document 9: OHNO, Shigeo and NISHIMURA, Yoshifumi (1997), "Tanpakushitsu Jikken Purotokoru (Protocols for Protein Experiments) 1—Functional Analysis Part", Shujunsha Co., Ltd.

Reference Document 10: OHNO, Shigeo and NISHIMURA, Yoshifumi (1997), "Tanpakushitsu Jikken Purotokoru (Protocols for Protein Experiments) 2—Structural Analysis Part", Shujunsha Co., Ltd.

Reference Document 11: ARISAKA, Fumio (2004) "Bioscience no Tame no Tanpakusitsukagaku Nyumon (Introduction to Protein Science for Bioscience)", Shokabo Co., Ltd.

Reference Document 12; T. Tamada, E. Honjo, Y. Maeda, T. Okamoto, M. Ishibashi, M. Tokunaga, and R. Kuroki, Proc. Natl. Acad. Sci. U.S.A, 2006, 103, 3135-40.

(SEQ ID NO Description List)
SEQ ID NO: 1: amino acid sequence of linear control G-CSF
SEQ ID NO: 2: amino acid sequence of G-CSF(C177)
SEQ ID NO: 3: amino acid sequence of G-CSF(C170)
SEQ ID NO: 4: amino acid sequence of G-CSF(C166)
SEQ ID NO: 5: amino acid sequence of G-CSF(C163)
SEQ ID NO: 6: amino acid sequence of cyclized G-CSF (C177)
SEQ ID NO: 7: amino acid sequence of cyclized G-CSF (C170)
SEQ ID NO: 8: amino acid sequence of cyclized G-CSF (C166)
SEQ ID NO: 9: amino acid sequence of cyclized G-CSF (C163)
SEQ ID NO: 10: amino acid sequence of G-CSF(C177) linked to DnaE
SEQ ID NO: 11: amino acid sequence of cyclized G-CSF (C170) linked to DnaE
SEQ ID NO: 12: amino acid sequence of cyclized G-CSF (C166) linked to DnaE
SEQ ID NO: 13: amino acid sequence of G-CSF(C163) linked to DnaE
SEQ ID NO: 14: amino acid sequence of filgrastim
SEQ ID NO: 15: amino acid sequence of DnaE-C
SEQ ID NO: 16: amino acid sequence of DnaE-N
SEQ ID NO: 17: nucleotide sequence of G-CSF(C177)
SEQ ID NO: 18: nucleotide sequence of G-CSF(C170)
SEQ ID NO: 19: nucleotide sequence of G-CSF(C166)
SEQ ID NO: 20: nucleotide sequence of G-CSF(C163)
SEQ ID NO: 21: nucleotide sequence of G-CSF(C177) linked to DnaE
SEQ ID NO: 22: nucleotide sequence of cyclized G-CSF (C170) linked to DnaE
SEQ ID NO: 23: nucleotide sequence of cyclized G-CSF (C166) linked to DnaE
SEQ ID NO: 24: nucleotide sequence of G-CSF(C163) linked to DnaE
SEQ ID NO: 25: nucleotide sequence of linear control G-CSF
SEQ ID NO: 26: primer sequence for amplifying the nucleotide sequence of linear control G-CSF
SEQ ID NO: 27: primer sequence for amplifying the nucleotide sequence of linear control G-CSF
SEQ ID NO: 28: nucleotide sequence encoding, in sequence, DnaE-C and DnaE-N
SEQ ID NO: 29: primer sequence for amplifying the nucleotide sequence of G-CSF(C177)
SEQ ID NO: 30: primer sequence for amplifying the nucleotide sequence of G-CSF(C177)
SEQ ID NO: 31: primer sequence for amplifying the nucleotide sequence of G-CSF(C170)
SEQ ID NO: 32: primer sequence for amplifying the nucleotide sequence of G-CSF(C170)
SEQ ID NO: 33: primer sequence for amplifying the nucleotide sequence of G-CSF(C166)
SEQ ID NO: 34: primer sequence for amplifying the nucleotide sequence of G-CSF(C166)
SEQ ID NO: 35: primer sequence for amplifying the nucleotide sequence of G-CSF(C163)
SEQ ID NO: 36: primer sequence for amplifying the nucleotide sequence of G-CSF(C163)

We claim:

1. A cyclized mutant granulocyte colony-stimulating factor (G-CSF) in which a linear control G-CSF protein consisting of an amino acid sequence set forth in SEQ ID NO: 1 is modified and cyclized, wherein the cyclized mutant G-CSF has an amino acid sequence selected from the group consisting of:
   (i) an amino acid sequence in which a serine or cysteine residue is added to the N-terminus of the amino acid sequence set forth in SEQ ID NO: 1, and an amino acid residue other than proline is added to the C-terminus of the amino acid sequence set forth in SEQ ID NO: 1;
   (ii) an amino acid sequence in which the first four amino acid residues are deleted from the N-terminus of the amino acid sequence set forth in SEQ ID NO: 1 and a serine or cysteine residue is added to the N-terminus of the amino acid sequence in which the four amino acid residues are deleted, and the last three amino acid residues are deleted from the C-terminus of the amino acid sequence set forth in SEQ ID NO: 1 and an amino acid residue other than proline is added to the C-terminus of the amino acid sequence in which the three amino acid residues are deleted;
   (iii) an amino acid sequence in which the first eight amino acid residues are deleted from the N-terminus of the amino acid sequence set forth in SEQ ID NO: 1 and a serine or cysteine residue is added to the N-terminus of the amino acid sequence in which the eight amino acid residues are deleted, and the last three amino acid residues are deleted from the C-terminus of the amino acid sequence set forth in SEQ ID NO: 1 and an amino acid residue other than proline is added to the C-terminus of the amino acid sequence in which the three amino acid residues are deleted; and
   (iv) an amino acid sequence in which the first eleven amino acid residues are deleted from the N-terminus of the amino acid sequence set forth in SEQ ID NO: 1 and a serine or cysteine residue is added to the N-terminus of the amino acid sequence in which the eleven amino acid residues are deleted, and the last three amino acid residues are deleted from the C-terminus of the amino acid sequence set forth in SEQ ID NO: 1 and an amino acid residue other than proline is added to the C-terminus of the amino acid sequence in which the three amino acid residues are deleted.

2. The cyclized mutant G CSF according to claim 1, wherein the mutant G-CSF consists of a cyclized amino acid sequence set forth in any one of SEQ ID NOs: 6 to 9.

3. A pharmaceutical composition comprising, as an active ingredient, the mutant G-CSF according to claim 1.

4. A pharmaceutical composition for treatment of neutropenia, comprising, as an active ingredient, the mutant G-CSF according to claim 1.

5. A method for producing the cyclized mutant protein according to claim 1, comprising:
   producing a linear mutant protein using a transformant comprising a recombinant vector wherein the recombinant vector comprises a nucleic acid comprising a nucleotide sequence encoding an amino acid sequence of the linear mutant protein, wherein the linear mutant protein consists of an amino acid sequence in which secondary structure-free regions at an N-terminal portion and a C-terminal portion of an original protein with a specific three-dimensional structure are deleted and a predetermined number of amino acid residues is added to each of an N-terminus and a C-terminus of a secondary structure-forming portion of the original protein after the deletion; the predetermined number of amino acid residues is the number of amino acid residues, the number corresponding to the number of amino acids connecting secondary structures of N-terminal residues and C-terminal residues of a secondary structure-forming portion of another protein, the secondary structures being similar to those of the secondary structure-forming portion of the original protein; and the most N terminal amino acid residue and the most C terminal amino acid residue of the predetermined number of amino acid residues added are amino acid residues that enable the linear mutant protein to be subject to cyclization; and linking an N-terminus and a C-terminus of the linear mutant protein by a chemical or biological method.

* * * * *

UNITED STATES PATENT AND TRADEMARK OFFICE
CERTIFICATE OF CORRECTION

PATENT NO. : 11,673,929 B2
APPLICATION NO. : 16/046276
DATED : June 13, 2023
INVENTOR(S) : Honda et al.

It is certified that error appears in the above-identified patent and that said Letters Patent is hereby corrected as shown below:

In the Specification

Column 18, Line 15: Please correct "DH5a" to read --DH5α--

Column 22, Line 40: Please correct "DH5a" to read --DH5α--

Column 22, Line 63: Please correct "DH5a" to read --DH5α--

Column 23, Lines 15-16: Please insert a paragraph break between "ligase" and "*E. coli*"

Column 23, Line 16: Please correct "DH5a" to read --DH5α--

Column 23, Line 18: Please correct "1004 ml" to read --100 μg/ml--

Signed and Sealed this
Fifteenth Day of August, 2023

Katherine Kelly Vidal
*Director of the United States Patent and Trademark Office*